US009840503B2

(12) United States Patent
Sun et al.

(10) Patent No.: US 9,840,503 B2
(45) Date of Patent: Dec. 12, 2017

(54) HETEROCYCLIC COMPOUNDS AND USES THEREOF

(71) Applicant: Incyte Corporation, Wilmington, DE (US)

(72) Inventors: Yaping Sun, Lansdale, PA (US); Yun-Long Li, Late of Chadds Ford, PA (US); David M. Burns, Glen Mills, PA (US)

(73) Assignee: Incyte Corporation, Wilmington, DE (US)

(*) Notice: Subject to any disclaimer, the term of this patent is extended or adjusted under 35 U.S.C. 154(b) by 0 days.

(21) Appl. No.: 15/151,259

(22) Filed: May 10, 2016

(65) Prior Publication Data
US 2016/0333008 A1 Nov. 17, 2016

Related U.S. Application Data

(60) Provisional application No. 62/159,732, filed on May 11, 2015.

(51) Int. Cl.
C07D 471/04 (2006.01)
A61K 31/519 (2006.01)

(52) U.S. Cl.
CPC .................. C07D 471/04 (2013.01)

(58) Field of Classification Search
None
See application file for complete search history.

(56) References Cited

U.S. PATENT DOCUMENTS

| | | |
|---|---|---|
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0015937 A1 | 1/2012 | Ding et al. |
| 2012/0088768 A1 | 4/2012 | Singh et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0184535 A1 | 7/2012 | Brzozka et al. |
| 2012/0219522 A1 | 8/2012 | Xi |
| 2012/0230993 A1 | 9/2012 | Graham et al. |
| 2012/0264740 A1 | 10/2012 | Goff et al. |
| 2012/0283261 A1 | 11/2012 | Bearss et al. |
| 2013/0018034 A1 | 1/2013 | Yao et al. |
| 2013/0018051 A1 | 1/2013 | Singh et al. |
| 2013/0045963 A1 | 2/2013 | Rodgers et al. |
| 2013/0059835 A1 | 3/2013 | Li et al. |
| 2013/0090330 A1 | 4/2013 | Ding et al. |
| 2013/0197070 A1 | 8/2013 | De Franciscis et al. |
| 2013/0281468 A1 | 10/2013 | Goff et al. |
| 2014/0005166 A1 | 1/2014 | Rodgers et al. |
| 2014/0018365 A1 | 1/2014 | Schultz-Fademrecht et al. |
| 2014/0121198 A1 | 5/2014 | Li et al. |
| 2014/0128400 A1 | 5/2014 | Singh et al. |
| 2014/0275023 A1 | 9/2014 | Namdev et al. |
| 2017/0044164 A1 | 2/2017 | Li et al. |
| 2017/0057965 A1 | 3/2017 | Li et al. |

FOREIGN PATENT DOCUMENTS

| | | |
|---|---|---|
| CN | 102408411 | 4/2012 |
| EP | 2465505 | 6/2012 |
| EP | 2484679 | 8/2012 |
| WO | WO 2004035580 | 4/2004 |
| WO | WO 2005025515 | 3/2005 |
| WO | WO 2006046023 | 5/2006 |
| WO | WO 2007/061737 | 5/2007 |
| WO | WO 2007/070514 | 6/2007 |
| WO | WO 2007120752 | 10/2007 |
| WO | WO 2007125315 | 11/2007 |
| WO | WO 2008076392 | 6/2008 |
| WO | WO 2009023269 | 2/2009 |
| WO | WO 2009/047514 | 4/2009 |
| WO | WO 2009/053737 | 4/2009 |
| WO | WO 2009/054864 | 4/2009 |
| WO | WO 2009085185 | 7/2009 |
| WO | WO 2009087225 | 7/2009 |
| WO | WO 2009/127417 | 10/2009 |
| WO | WO 2010/005876 | 1/2010 |
| WO | WO 2010/005879 | 1/2010 |
| WO | WO 2010008454 | 1/2010 |
| WO | WO 2010/014755 | 2/2010 |
| WO | WO 2010025073 | 3/2010 |
| WO | WO 2010071885 | 6/2010 |
| WO | WO 2010/090764 | 8/2010 |
| WO | WO 2011038185 | 3/2011 |
| WO | WO 2011/045084 | 4/2011 |
| WO | WO 2011/139273 | 11/2011 |

(Continued)

OTHER PUBLICATIONS

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.

Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk , 1975, 137-41 (English abstract only).

Cecil Textbook of Medicine, edited by Bennet, J.C., and Plum F., 20th edition, vol. 1, 1004-1010, 1996.

Chung et al., "Synthesis of certain [6:5:6] linear tricyclic nucleosides as potential antitumor agents," Journal of Medicinal Chemistry, Nov. 1980, 23(11): 1158-66.

Cohen., ""The development and therapeutic potential of protein kinase inhibitors,"" Current Opinion in Chemical Biology, 1999, 3: 459-465, 1999.

Dermer et al., "Another Anniversary for the War on Cancer," Bio/Technology, Mar. 1994, 12: 320.

(Continued)

Primary Examiner — Brian J Davis
(74) Attorney, Agent, or Firm — Fish & Richardson P.C.

(57) ABSTRACT

The present disclosure relates to heterocyclic compounds, and pharmaceutical compositions of the same, that are inhibitors of the TAM protein kinases and are useful in the treatment of TAM-associated diseases such as cancer.

28 Claims, No Drawings

(56) References Cited

FOREIGN PATENT DOCUMENTS

| WO | WO 2012/028332 | 3/2012 |
|---|---|---|
| WO | WO 2012048129 | 4/2012 |
| WO | WO 2012129344 | 9/2012 |
| WO | WO 2012/135800 | 10/2012 |
| WO | WO 2013/052417 | 4/2013 |
| WO | WO 2013/074633 | 5/2013 |
| WO | WO 2013085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014109858 | 7/2014 |
| WO | WO 2014/164729 | 10/2014 |
| WO | WO 2015/012298 | 1/2015 |
| WO | WO 2015/068767 | 5/2015 |
| WO | WO 2016/097918 | 6/2016 |
| WO | WO 2017/027717 | 2/2017 |
| WO | WO 2017/062797 | 4/2017 |
| WO | WO 2017/083788 | 5/2017 |
| WO | WO 2017/083789 | 5/2017 |

OTHER PUBLICATIONS

Dodonova et al., "Synthesis of 4-aryl-, 2, 4-diaryl-and 2, 4, 7-trialylpyrrolo [2, 3-d] pyrimidines by a combination of the Suzuki cross-coupling and N-arylation reactions," Tetrahedron, 2012, 68(1):329-339.

Freshney et al., "Culture of Animal Cells," A Manual of Basic Technique, Alan R. Liss, Inc., 1983, New York, p. 4.

Ghosh, "Synthesis of 4-oxazolinephenylboronic acid and heterobiaryl oxazolines via a Suzuki reaction," Journal of Chemical Research, Apr. 2009, 4:205-207.

Golub et al., "Molecular Classification of Cancer: Class Discovery and Class Prediction by Gene Expression Monitoring," Science, 1999, 286: 531-537.

International Search Report and Written Opinion in International Application No. PCT/US2016/046574, dated Oct. 21, 2016, 14 pages.

International Search Report and Written Opinion in International Application No. PCT/US2016/048716, dated Nov. 2, 2016, 12 pages.

Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.

Klimke and Ludemann, "Further evidence for a S-syn correlation in the purine (β) ribosides: the solution conformation of two tricyclic analogs of adenosine and guanosine," Journal of Biosciences, 1979, 34C(9-10): 653-7.

Lemke, "Biology of the TAM Receptors," Cold Spring Harb Perspect Biol., 2013, 5: 1-17.

Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.

Liu et al., "UNC1062, a new and potent Mer inhibitor," European Journal of Medicinal Chemistry, 2013, 65: 83-93.

Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.

Singer et al., "Photochromism of Diarylethene-Functionalized 7-Deazaguanosines," European Journal of Organic Chemistry, 2013, 14: 2766-2769.

Skardziute, "Optical study of the formation of pyrrolo[2,3-d]pyrimidine-based fluorescent nanoaggregates," Tetrahedron, 2013, 69(46):9566-9572.

Strassmaier and Karpen, "Novel N7- and N1-Substituted cGMP Derivatives Are Potent Activators of Cyclic Nucleotide-Gated Channels," Journal of Medicinal Chemistry, Aug. 2007, 50: 4186-4194.

Tumkevicius, "Pyrrolo [2, 3-d] pyrimidine-Core-Extended π-Systems: Synthesisof 2, 4, 7-Triatylpyrrolo [2, 3-d] pyrimidines," Synlett, 2011, 12:1705-1708.

Tumkevicius, "Synthesis and photophysical properties of oligoarylenes with a pyrrolo [2, 3-d] pyrimidine core," Tetrahedron Letters (2010), 51(30), 3902-3906.

Urbonas et al., ""A Novel Highly Site-Selective Synthesis of 2,4,7-Triarylpyrrolo[2,3-d] pyrimidines by a Combination of Palladium(0)-, Nickel(0)-, and Copper(I)-Catalyzed Cross-Coupling Reactions,"" Synlett, 2013, 24(11):1383-1386.

Yamazoe et al., "Mechanism of formation and structural characterization of DNA adducts derived from peroxidative activation of benzidine," Carcinogenesis, Sep. 1988, 9(9): 1635-41.

Zhao, et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.

Zhou et al., "Synthesis and evaluation of Janus type nucleosides as potential HCV NS5B polymerase inhibitors," Bioorganic & Medicinal Chemistry Letters, Jun. 2013, 23: 3385-3388.

Burbridge et al., "S49076 Is a Novel Kinase Inhibitor of MET, AXL, and FGFR with Strong Preclinical Activity Alone and in Association with Bevacizumab," AACR Journals, 2013, 1749-1762.

Berge, "Pharmaceutical Salts," Journal of Pharmaceutical Science, 66, 2 (1977).

Blom et al., "Optimizing Preparative LC/MS Configurations and Methods for Parallel Synthesis Purification," J. Comb. Chem., 2003, 5: 670-683.

Blom et al., "Preparative LC-MS Purification: Improved Compound-Specific Method Optimization," J. Comb. Chem., 2004, 6: 874-883.

Blom, "Two-Pump at-Column-Dilution Configuration for Preparative Liquid Chromatography-Mass Spectrometry," J. Comb. Chem., 2002, 4: 295-301.

Chambers et al., "Lymphoproliferation in CTLA-4-deficient mice is mediated by costimulation-dependent activation of CD4+ T cells," Immunity, Dec. 1997, 7(6): 885-95.

Cook et al., "MerTK inhibition in tumor leukocytes decreases tumor growth and metastasis," J. Clin. Invest., Aug. 2013, 123(9): 3231-42.

Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.

Feneyrolles et al., "Axl kinase as a key target for oncology: focus on small molecule inhibitors," Mol Cancer Therapy, Sep. 2014, 13(9): 2141-8.

Graham et al., "Cloning and developmental expression analysis of the murine c-mer tyrosine kinase," Oncogene, Jun. 1995, 10(12): 2349-59.

Graham et al., "The TAM family: phosphatidylserine sensing receptor tyrosine kinases gone awry in cancer," Nat. Rev. Cancer, Dec. 2014, 14(12): 769-85.

Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.

Huang et al., "Structural insights into the inhibited states of the Mer receptor tyrosine kinase," Journal of Structural Biology, 2009, 165: 88-96.

International Search Report and Written Opinion in International Application No. PCT/US2016/031625, dated Jul. 7, 2016, 11 pages.

Koorstra et al., "The Axl receptor tyrosine kinase confers an adverse prognostic influence in pancreatic cancer and represents a new threapeutic target," Cancer Biol. Ther., Apr. 2009, 8(7): 618-26.

Lai and Lemke, "An extended family of protein-tyrosine kinase genes differentially expressed in the vertebrate nervous system," Neuron, May 1991, 6(5): 691-704.

Lee-Sherick et al., "Aberrant Mer receptor tyrosine kinase expression contributes to leukemogenesis in acute myeloid leukemia," Oncogene, Nov. 2013, 32(46): 5359-68.

Lew et al., "Differential TAM receptor-ligand-phospholipid interactions delimit differential TAM bioactivities," Elife, Sep. 2014, e03385.

(56) References Cited

OTHER PUBLICATIONS

Li et al., "Axl as a potential therapeutic target in cancer: role of Axl in tumor growth, metastasis and angiogenesis," Oncogene, Oct. 2009, 28(39): 3442-55.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-31.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases: Biologic Functions, Signaling, and Potential Therapeutic Targeting in Human Cancer," Adv. Cancer Research, 2008, 100: 35-83.
Liu et al., "Discovery of Novel Small Molecule Mer Kinase Inhibitors for the Treatment of Pediatric Acute Lymphoblastic Leukemia," ACS Med. Chem. Lett., 2012, 3(2): 129-134.
Liu et al., "Discovery of Novel Small Molecule Mer Kinase Inhibitors for the Treatment of Pediatric Acute Lymphoblastic Leukemia," Supporting Information, 53 pages, (2012).
Liu et al., "Discovery of Small Molecule Mer Kinase Inhibitors for the Treatment of Pediatric Acute Lymphoblastic Leukemia," ACS Medicinal Chemistry Letters, 2012, 3: 129-134.
Lu and Lemke, "Homeostatic regulation of the immune system by receptor tyrosine kinases of the Tyro 3 family," Science, Jul. 2001, 293(5528): 306-11.
Mollard et al., "Design, Synthesis, and Biological Evaluation of a Series of Novel AXL Kinase Inhibitors," ACS Medicinal Chemistry Letters, 2011, 2: 907-912.
Nishimura et al., "Autoimmune dilated cardiomyopathy in PD-1 receptor-deficient mice," Science, 2001, 291(5502): 319-22.
O'Bryan et al., "axl, a transforming gene isolated from primary human myeloid leukemia cells, encodes a novel receptor tyrosine kinase," Mol. Cell Biol., Oct. 1991, 11(10): 5016-31.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Remington's Pharmaceutical Sciences, 17th ed., Mack Publishing Company, Easton, PA., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Schlegel et al., "MERTK receptor tyrosine kinase is a therapeutic target in melanoma," The Journal of Clinical Investigation, May 2013, 123(5): 2257-2267.
Schroeder et al., "Discovery of N-(4-(2-Amino-3-chloropyridin-4-yloxy)-3-fluorophenyl)-4-ethoxy-1-4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.
Suarez et al., "Inhibitors of the TAM subfamily of tyrosine kinsases: Synthesis and biological evaluation," European Journal of Medicinal Chemistry, 2013, 61: 2-25.
Tai et al., "Axl promotes cell invasion by inducing MMP-9 activity through activation of NF-kappaB and Brg-1," Oncogene, Jul. 2008, 27(29): 4044-55.
Traore et al., "New aminopyrimidine derivatives as inhibitors of the TAM family," European Journal of Medicinal Chemistry, 2013, 70: 789-801.
Waizeneggar et al., "Role of Growth arrest-specific gene 6-Mer axis in multiple myeloma," Leukemia, 2015, 29: 696-704.
Wang et al., "Mer receptor tyrosine kinase promotes invasion and survival in glioblastoma multiforme," Oncogene, Feb. 2013, 32(7): 872-82.
Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Zhang et al., "Activation of the AXL kinase causes resistance to EGFR-targeted therapy in lung cancer," Nat. Genet., 2012, 44(8): 852-60.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.
Zhang et al., "UNC20205, a Potent and Orally Bioavailable MER/FLT3 Dual Inhibitor," Journal of Medicinal Chemistry, 2014, 57: 7031-7041.
Angelillo-Scherrer et al., "Role of Gas6 in erythropoiesis and anemia in mice," J. Clin. Invest., 2008, 118: 583-596.
Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
Borovik et al., "Synthesis of 2-substituted pyrimido[4,5-b]indoles and N-pheny1-2,2-diethoxy-3-arylideneindolines," v sb., Khimiya i Farmakol. Indol'n. Soedinenii, 1975, 50 (English abstract only).
Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.
International Search Report and Written Opinion in International Application No. PCT/US2017/024270, dated Jun. 14, 2017, 18 pages.
Kerekes et al., "Aurora kinase inhibitors based on the imidazo[1,2-a]pyrazine core: fluorine and deuterium incorporation improve oral absorption and exposure," J. Med. Chem., 2011, 54: 201-210.
Myers et al., "AXL inhibitors in cancer: A medicinal chemistry perspective," Journal of Medicinal Chemistry, 2015, pp. 3593-3608.
Shibata et al., "Axl receptor blockade ameliorates pulmonary pathology resulting from primary viral infection and viral exacerbation of asthma," The Journal of Immunology, 2014, 192: 3569-3581.
Xu et al., "Design, synthesis and biological evaluation of deuterated nintedanib for improving pharmacokinetic properties," J. Label Compd. Radiopharm., 2015, 58: 308-312.

HETEROCYCLIC COMPOUNDS AND USES THEREOF

This application claims the benefit of priority of U.S. Provisional Application No. 62/159,732, filed May 11, 2015, which is incorporated herein by reference in its entirety.

FIELD OF THE INVENTION

This disclosure relates to compounds or ligands that modulate or inhibit TAM kinases, and to methods for use thereof. The information provided is intended solely to assist the understanding of the reader. None of the information provided nor references cited is admitted to be prior art to the present invention. Each of the references cited is incorporated herein in its entirety and for any purpose.

BACKGROUND OF INVENTION

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells. Accordingly, there is a need in the art for compounds and methods of use thereof for the modulation of TAM kinases in treatment of cancer.

SUMMARY OF INVENTION

In one aspect, the present disclosure relates to compounds having Formula (I):

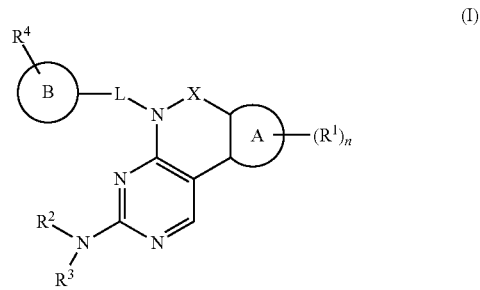

(I)

or a pharmaceutically acceptable salt a tautomer or an isomer thereof, wherein constituent variables are defined herein.

In another aspect, the present disclosure provides pharmaceutical compositions comprising a compound of Formula (I), or a pharmaceutically acceptable salt, a tautomer or an isomer thereof, and at least one pharmaceutically acceptable carrier or excipient.

In another aspect, the present disclosure provides methods for inhibiting TAM kinases. The method includes contacting the TAM kinases with a compound of Formula (I), or a pharmaceutically acceptable salt, a tautomer or an isomer thereof or a composition comprising compounds of Formula (I).

In another aspect, the present disclosure provides a method for treating a disease associated with abnormal activity or expression of TAM kinases. The method includes administering an effective amount of a compound of Formula (I), or a pharmaceutically acceptable salt, a tautomer or an isomer thereof, or a composition comprising a compound of Formula (I), to a patient in need thereof.

In yet another aspect, the present disclosure provides compounds of Formula (I) for use in treating a disease associated with abnormal activity or expression of TAM kinases.

In another aspect, the present disclosure provides a method for treating a disorder mediated by TAM kinases, or a mutant thereof, in a patient in need thereof. The method includes administering to the patient a compound as described herein or pharmaceutically acceptable salts thereof or a composition comprising a compound as described herein.

In another aspect, the present disclosure provides the use of compounds of Formula (I) in the preparation of a medicament for use in therapy.

DETAILED DESCRIPTION

Compounds

In one aspect, the present disclosure provides a compound having Formula (I):

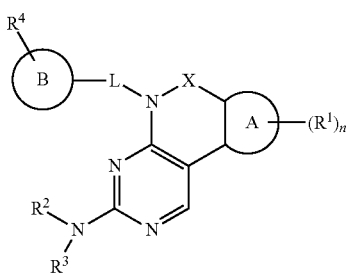

(I)

or a pharmaceutically acceptable salt, a tautomer or an isomer thereof, wherein:

ring A is fused $C_{6-10}$ aryl, fused 5- or 6-membered heteroaryl or fused 4 to 10-membered heterocycloalkyl, wherein the fused 5- or 6-membered heteroaryl or fused 4 to 10-membered heterocycloalkyl has a carbon and 1-4 heteroatoms as ring members selected from O, N, and S, wherein the N and S as ring members are each optionally oxidized, with the proviso that ring A is other than pyrazolyl having the formula

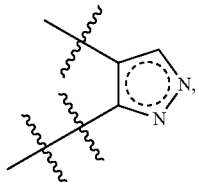

wherein the single wavy line indicates the point of attachment to the X linkage in Formula (I), the double wavy line indicates the point of attachment to the ring carbon atom of the pyrimidine ring in Formula (I) and the dashed circular line indicates a single or a double bond and wherein a ring carbon in pyrazolyl is optionally replaced by a carbonyl group;

ring B is $C_{6-10}$ aryl, 5- or 6-membered heteroaryl, $C_{3-6}$ cycloalkyl or 4 to 10-membered heterocycloalkyl, wherein 5- or 6-membered heteroaryl or 4 to 10-membered heterocycloalkyl has a carbon and 1-4 heteroatoms as ring members selected from O, N and S, wherein the N and S as ring members are each optionally oxidized and a ring carbon in ring B is optionally replaced by a carbonyl group;

L is a bond, $(CR^5R^6)_m$—, —C(O)—, —S(O) or $SO_2$—;
$R^5$ and $R^6$ are each independently selected from H, $C_{1-4}$alkyl, $C_{1-4}$ alkoxy, $C_{1-4}$haloalkyl, $C_{1-4}$haloalkoxy, halogen, OH, CN and $NH_2$, wherein $C_{1-4}$alkyl, $C_{1-4}$ alkoxy, $C_{1-4}$haloalkyl and $C_{1-4}$haloalkoxy of $R^5$ and $R^6$ are each further optionally substituted with from 1-2 members independently selected from halo, OH, CN, $NH_2$, $OR^7$, $C_{1-4}$alkyl, $C_{1-4}$ alkoxy, $C_{1-4}$ haloalkyl and $C_{1-4}$ haloalkoxy, or $R^5$ and $R^6$ taken together with the carbon atom to which they are attached form a $C_{3-6}$ cycloalkyl ring, optionally substituted with 1-2 members independently selected from OH, CN, $NH_2$, $OR^7$, $C_{1-4}$ alkyl, $C_{1-4}$ alkoxy, $C_{1-4}$haloalkyl or $C_{1-4}$haloalkoxy;

each $R^7$ is independently $C_{1-4}$alkyl;
the subscript m is 1, 2 or 3;
X is a bond, —C(O)— or —$CR^8R^9$—;
$R^8$ and $R^9$ are each independently H, $C_{1-4}$alkyl, $C_{1-4}$ alkoxy, $C_{1-4}$haloalkyl or $C_{1-4}$haloalkoxy, wherein $C_{1-4}$alkyl, $C_{1-4}$ alkoxy, $C_{1-4}$haloalkyl and $C_{1-4}$haloalkoxy of $R^8$ and $R^9$ are each optionally substituted with 1-2 members independently selected from OH, CN, $NH_2$, $OR^7$, $NHR^7$, $NR^7R^7$, $C_{1-4}$ alkyl, $C_{1-4}$ alkoxy, $C_{1-4}$haloalkyl, and $C_{1-4}$haloalkoxy;

or $R^8$ and $R^9$ taken together with the carbon atom to which they are attached form a $C_{3-6}$ cycloalkyl ring, optionally substituted with from 1-2 members independently selected from OH, CN, $NH_2$, $OR^7$, $NHR^7$, $NR^7R^7$, $C_{1-4}$alkyl, $C_{1-4}$ alkoxy, $C_{1-4}$haloalkyl, and $C_{1-4}$haloalkoxy;

each $R^1$ is independently selected from H, halo, $C_{1-6}$ alkyl, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NH_2$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^1$ are each optionally substituted with 1, 2, 3, or 4 $R^b$ substituents;

each $R^b$ is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with from 1-3 $R^d$ substituents;

or two $R^1$ substituents attached to the same carbon of ring A are taken together to form an oxo group or a $C_{3-6}$cycloalkyl optionally substituted with from 1-2 members independently selected from OH, CN, $NH_2$, $OR^7$, $NHR^7$, $NR^7R^7$, $C_{1-4}$alkyl, $C_{1-4}$ alkoxy, $C_{1-4}$ haloalkyl, and $C_{1-4}$haloalkoxy;

each $R^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-4}$ alkyl, $C_{1-4}$ haloalkyl, halo, CN, $R^e$, $NHOR^e$, $OR^e$, $SR^e$, $C(O)R^e$, $C(O)NR^eR^e$, $C(O)OR^e$, $OC(O)R^e$, $OC(O)NR^eR^e$, $NH_2$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NH_2$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with from 1-3 $R^p$ substituents;

or any two $R^a$ substituents, together with the nitrogen atom to which they are attached, form a 4-, 5-, 6-, or 7-membered heterocycloalkyl group optionally substituted with 1, 2, or 3 $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{1-6}$ haloalkyl, halo, CN, $OR^i$, $R^i$, $SR^i$, $NHOR^i$, $C(O)R^i$, $C(O)NR^iR^i$, $C(O)ORS$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, and 5-6 membered heteroaryl of $R^h$ are each further optionally substituted by 1, 2, or 3 $R^j$ substituents;

each $R^j$ independently selected from halo, $C_{1-4}$ alkyl, $C_{1-4}$ haloalkyl, CN, $R^k$, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

or any two $R^c$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^e$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^g$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^i$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^k$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^o$ substituents, together with the nitrogen atom to which they are attached, form a 4-, 5-, 6-, or 7-membered heterocycloalkyl group optionally substituted with 1, 2, or 3 independently selected $R^h$ substituents;

each $R^e$, $R^i$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl and $C_{2-4}$ alkynyl of $R^e$, $R^i$, $R^k$, $R^o$ or $R^p$ are each optionally substituted with 1, 2, or 3 substituents independently selected from OH, CN, amino, halo, $C_{1-4}$ alkyl, $C_{1-4}$ alkoxy, $C_{1-4}$ alkylthio, $NHR^7$, $NHR^7$, $C_{1-4}$ haloalkyl, and $C_{1-4}$ haloalkoxy;

$R^2$ is $C_{1-6}$alkyl optionally substituted with from 1-3 independently selected $R^b$ groups;

$R^3$ is H or $C_{1-6}$alkyl;

$R^4$ is —$NH_2$, —NHOH, —OH, —CN, —COOH, $C_{1-4}$ alkyl, $C_{1-4}$ alkoxy, $C_{1-2}$ haloalkyl or $C_{1-2}$ haloalkoxy, —$NHR^{10}$, —$N(R^{10})_2$, $NHOR^{10}$, —$NHC(O)R^{10}$, —$C(O)R^{10}$, —$C(O)NR^{10}R^{10}$, —$C(O)OR^{10}$, —$OC(O)R^{10}$, —$OC(O)NR^{10}R^{10}$, —$NR^{10}R^{10}$, —$NR^{10}C(O)R^{10}$ or —$NR^{10}C(O)OR^{10}$; wherein the $C_{1-4}$ alkyl, $C_{1-4}$ alkoxy, $C_{1-2}$ haloalkyl and $C_{1-2}$ haloalkoxy of $R^4$ are each optionally substituted with from 1-3 $R^m$ substituents independently selected from OH, CN, amino, halo, $C_{1-4}$ alkyl, $C_{1-4}$ alkoxy, $C_{1-4}$ alkylthio, $NHR^7$, $NR^7R^7$, $C_{1-4}$ haloalkyl, and $C_{1-4}$ haloalkoxy;

each $R^{10}$ is independently $C_{1-4}$ alkyl, $C_{6-10}$aryl or $C_{1-2}$haloalkyl, each of which is optionally substituted with 1-2 independently selected $R^f$ groups; and the subscript n is 1, 2 or 3.

In some embodiments, compounds of Formula (I) have selective inhibitory activity on TAM protein kinases or any mutant thereof.

In some embodiments of compounds of Formula (I), ring A is fused $C_{6-10}$aryl or fused 5- or 6-membered heteroaryl having a carbon and 1-4 heteroatoms as ring members selected from O, N and S, with the proviso that ring A is other than pyrazolyl having the formula:

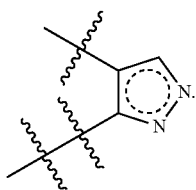

In certain embodiments, ring A is a fused $C_{6-10}$aryl. In one embodiment, ring A is fused phenyl.

In some embodiments of compounds of Formula (I), ring A is fused 5- or 6-membered heteroaryl having a carbon and 1-4 heteroatoms as ring members selected from O, N and S, with the proviso that ring A is other than pyrazolyl having the formula:

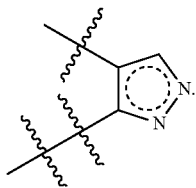

In certain embodiments, ring A is fused 5- or 6-membered heteroaryl other than fused pyrazolyl. In some embodiments, ring A is fused 5-membered heteroaryl other than fused pyrazolyl. In certain embodiments, ring A is fused 5-membered heteroaryl other than pyrazolyl having the formula:

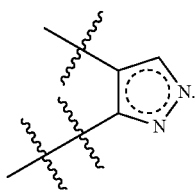

In some embodiments of compounds of Formula (I), ring A is fused 5-membered heteroaryl selected from:

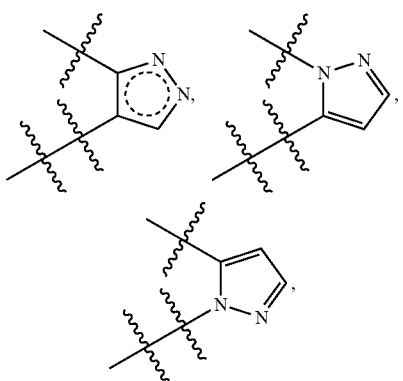

imidazolyl, triazolyl, tetrazolyl, oxazolyl, thiazolyl, isoxazolyl, furanyl, thiophenyl, and isothiazolyl. In certain instances, ring A is fused 5-membered heteroaryl selected from:

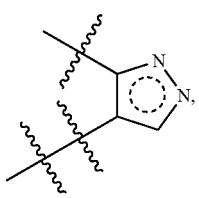

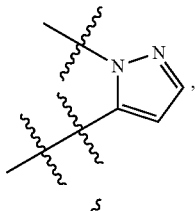

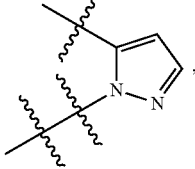

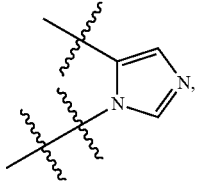

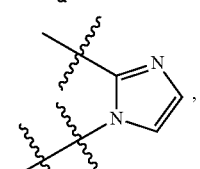

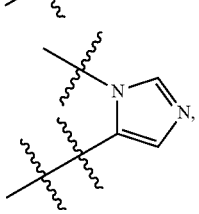

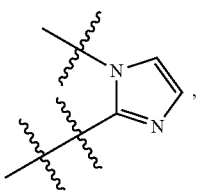

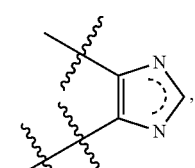

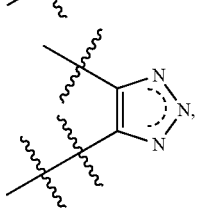

-continued
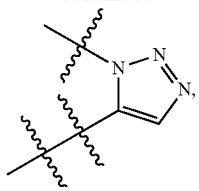
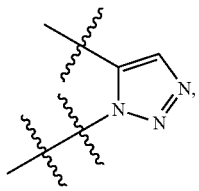
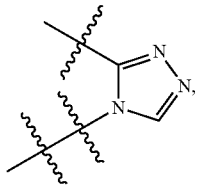
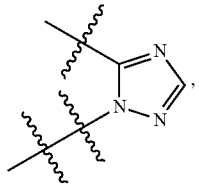
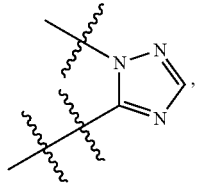
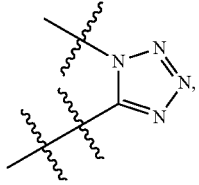
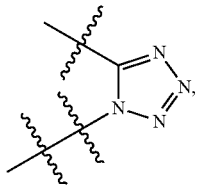
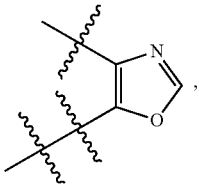
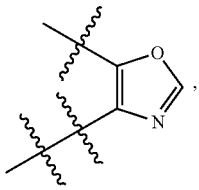
-continued
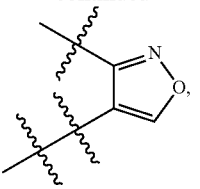
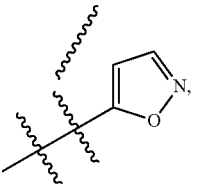
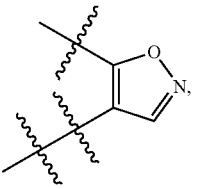
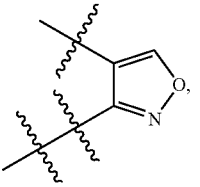
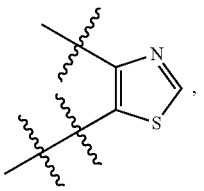
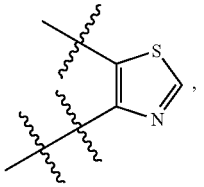
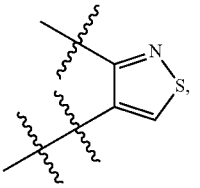
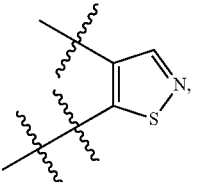
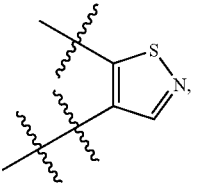

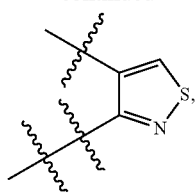

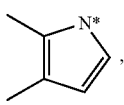

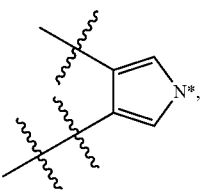

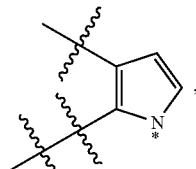

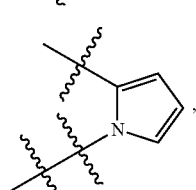

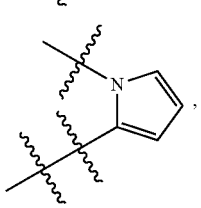

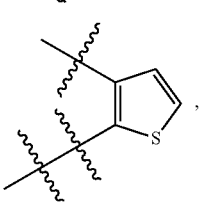

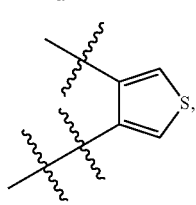

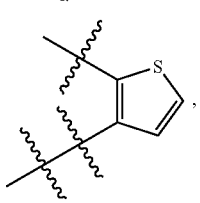

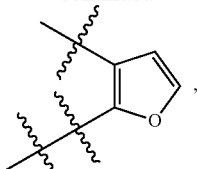

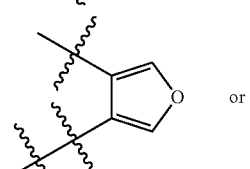

or

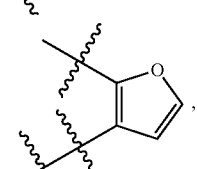

where the single wavy line indicates the point of attachment to the X linkage in Formula (I), the double wavy line indicates the point of attachment to the ring carbon atom of the pyrimidine ring in Formula (I), the dashed circular line indicates a single or a double bond and the asterisk symbol * on the nitrogen atom indicates the point of attachment to the $R^1$ group.

In some embodiments of compounds of Formula (I), ring A is fused 6-membered heteroaryl selected from pyridyl, pyrimidinyl, pyrazinyl, pyridazinyl and triazinyl. In certain instances, ring A is fused 6-membered heteroaryl selected from

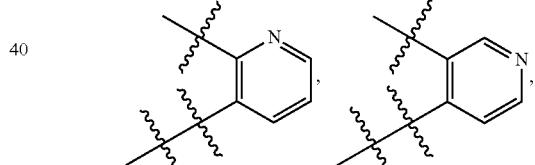

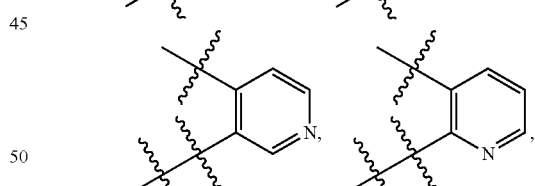

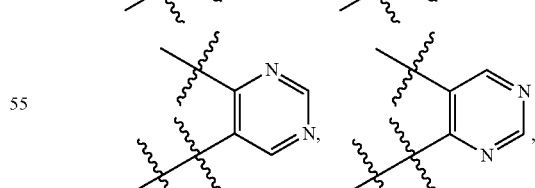

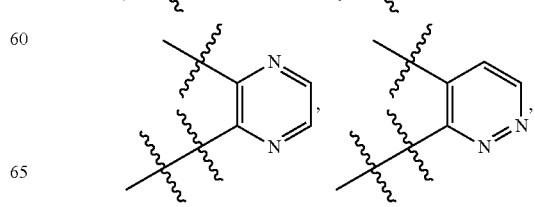

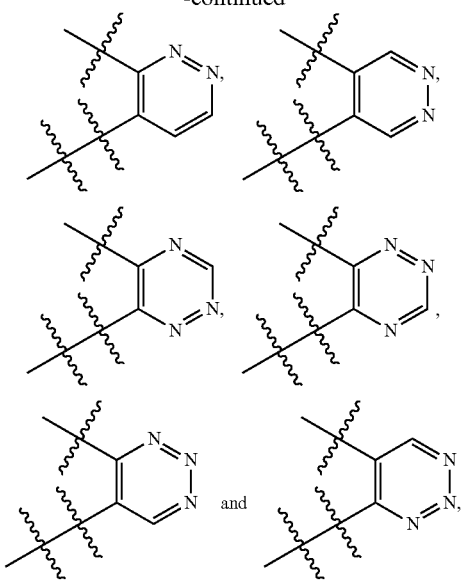

where the single wavy line indicates the point of attachment to the X linkage in Formula (I) and the double wavy line indicates the point of attachment to the ring carbon atom of the pyrimidine ring in Formula (I).

In some embodiments of compounds of Formula (I), ring A is fused 4 to 10-membered heterocycloalkyl. In certain embodiments, ring A is fused 4 to 6-membered heterocycloalkyl. In certain instances, ring A is fused heterocycloalkyl selected from

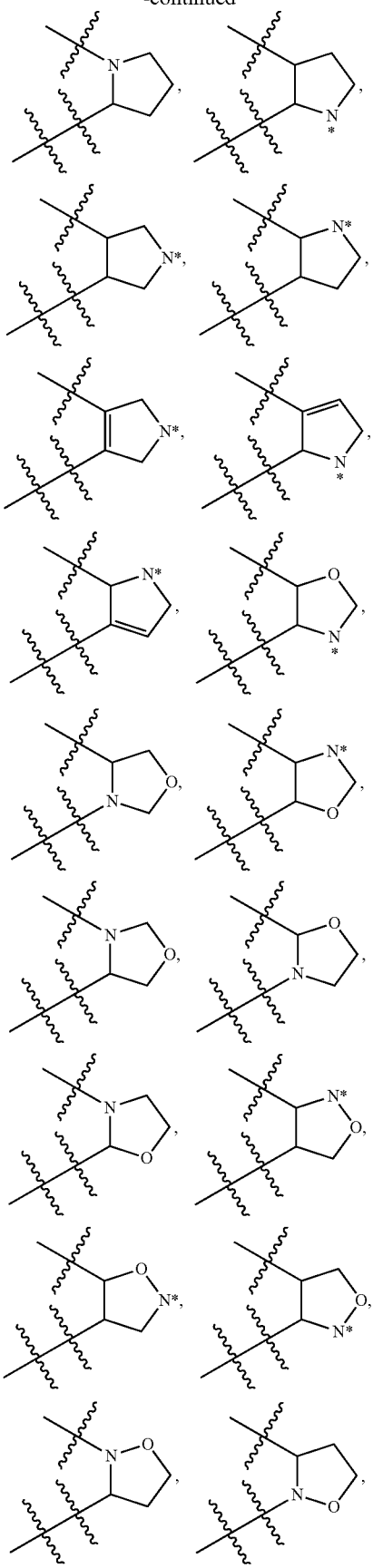

-continued
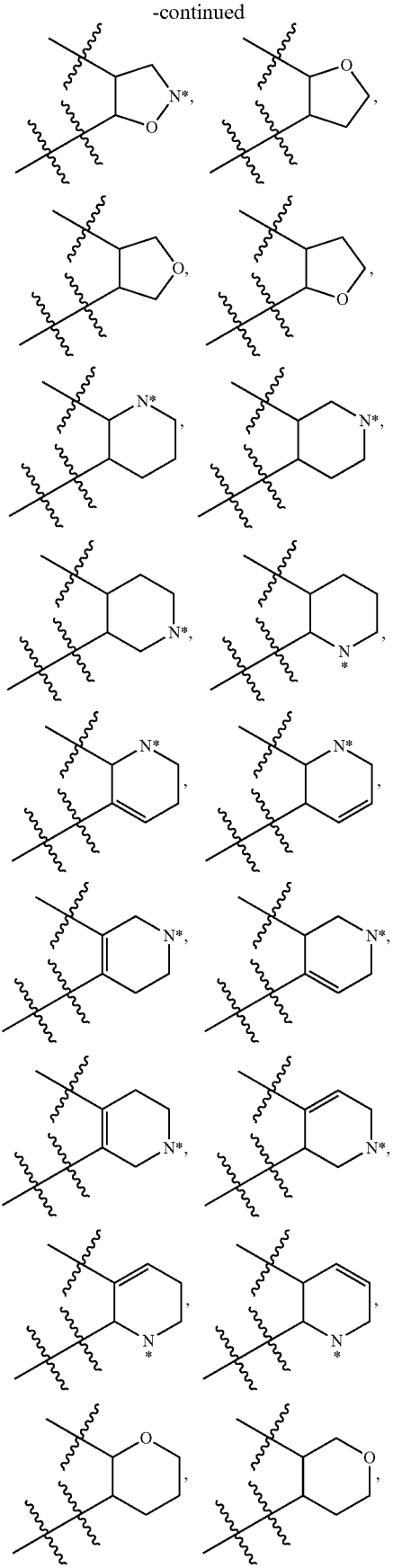
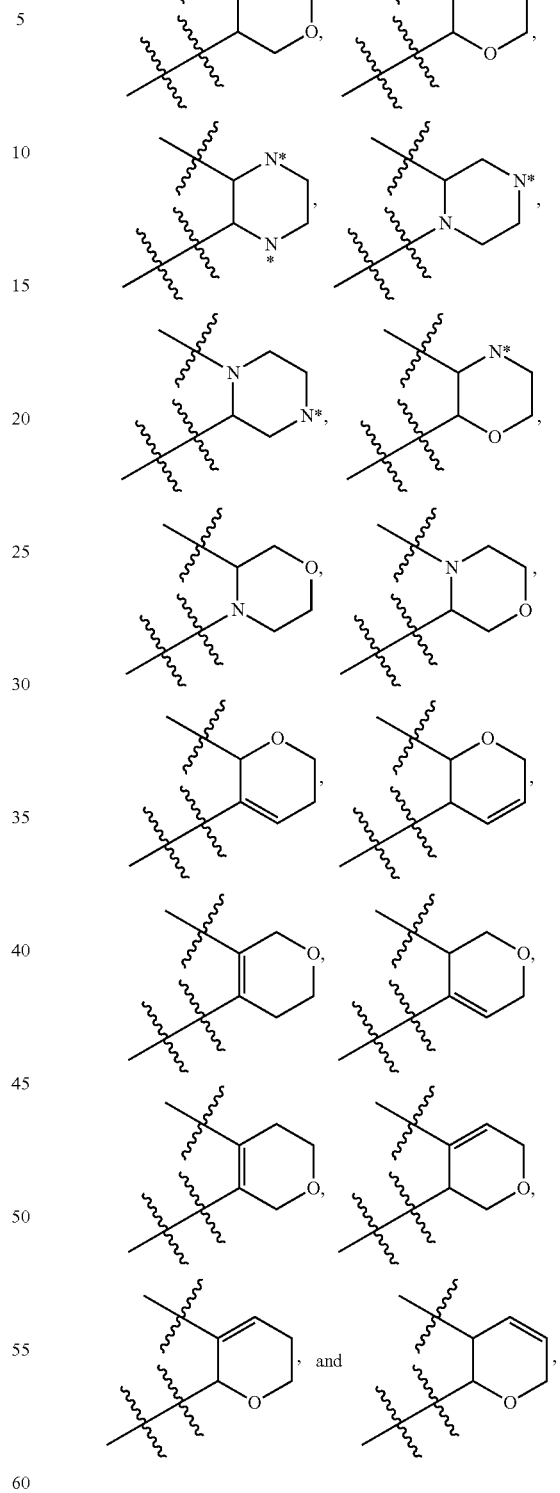
where the single wavy line indicates the point of attachment to the X linkage in Formula (I), the double wavy line indicates the point of attachment to the ring carbon atom of the pyrimidine ring in Formula (I) and the asterisk symbol * on the nitrogen atom indicates the point of attachment to $R^1$ group.

In some embodiments of compounds of Formula (I), ring B is $C_{6-10}$ aryl, 5- or 6-membered heteroaryl, $C_{3-6}$ cycloalkyl or 4 to 7-membered heterocycloalkyl, wherein 5- or 6-membered heteroaryl or 4 to 7-membered heterocycloalkyl has a carbon and 1-4 heteroatoms as ring members selected from O, N and S, wherein the N and S as ring members are each optionally oxidized and a ring carbon in ring B is optionally replaced by a carbonyl group.

In some embodiments of compounds of Formula (I), ring B is $C_{6-10}$aryl. In one embodiment, ring B is phenyl. In another embodiment, ring B is 1-naphthyl or 2-naphthyl.

In some embodiments of compounds of Formula (I), ring B is 5-membered heteroaryl selected from 1-pyrrolyl, 2-pyrrolyl, 3-pyrrolyl, 1-pyrazolyl, 3-pyrazolyl, 4-pyrazolyl, 1-imidazolyl, 2-imidazolyl, 4-imidazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1-H-5-tetrazolyl, 3H-5-tetrazolyl, 2-furanyl, 3-furanyl, 2-thiopenyl, and 3-thiophenyl.

In some embodiments of compounds of Formula (I), ring B is 6-membered heteroaryl selected from 2-pyridyl, 3-pyridyl, 4-pyridyl, 2-pyrazinyl, 3-pyridazinyl, 4-pyridazinyl, 2-pyrimidinyl, 4-pyrimidinyl, 5-pyrimidinyl, 1,2,3-triazin-4-yl, 1,2,3-triazin-5-yl, 1,3,5-triazin-2-yl, 1,2,4-triazin-3-yl, 1,2,4-triazin-5-yl, and 1,2,4-triazin-6-yl.

In some embodiments of compounds of Formula (I), ring B is $C_{3-6}$ cycloalkyl, where a ring carbon atom is optionally replaced by a carbonyl group. In some embodiments, ring B is $C_{3-6}$cycloalkyl. In certain embodiments, ring B is cyclopropyl, cyclobutyl, cyclopentyl or cyclohexyl. In other embodiments, ring B is 2-oxocyclohexyl, 3-oxocyclohexyl, 4-oxocyclohexyl, 2-oxocyclopentyl, 3-oxocyclopentyl or 2-oxocyclobutyl.

In some embodiments of compounds of Formula (I), ring B is 4 to 7-membered heterocycloalkyl, where a ring carbon atom is optionally replaced by a carbonyl group. In some embodiments, ring B is 4 to 7-membered heterocycloalkyl selected from azetidinyl, oxetanyl, pyrrolidinyl, tetrahydrofuranyl, oxazolidinyl, isooxazolidinyl, thiazolidinyl, isothiazolidinyl, tetrahydro-pyranyl, morpholinyl, piperidinyl, piperazinyl, oxepanyl or azepanyl. In certain instances, ring B is 2-oxetanyl, 2-tetrahydrofuranyl, 3-tetrahydrofuranyl, 2-tetrahydro-pyranyl, 3-tetrahydro-pyranyl, 4-tetrahydropyranyl, 3,6-dihydro-2H-pyranyl, 3,4-dihydro-2H-pyranyl, 1-azetidinyl, 2-azetidinyl, 3-azetidinyl, 1-pyrrolidinyl, 2-pyrrolidinyl, 3-pyrrolidinyl, 1-piperidinyl, 2-piperidinyl, 3-piperidinyl, 4-piperidinyl, 1-piperazinyl, 2-piperazinyl, 4-morpholinyl, 3-morpholinyl, 2-morpholinyl, 1-azepanyl, 2-azepanyl, 3-azepanyl, 4-azepanyl, 2-oxepanyl, 3-oxepanyl or 4-oxepanyl. In certain instances, ring B is 2-oxo-1-pyrrolidinyl, 2-oxo-1-piperidinyl, 2-oxopyrrolidin-3-yl, 2-oxopyrrolidin-4-yl, 2-oxo-piperidin-4-yl or 2-oxo-piperidin-5-yl.

In some embodiments of compounds of Formula (I), L is a bond, —$(CR^5R^6)_m$—, —C(O)—, —S(O) or —$SO_2$—, wherein $R^5$ and $R^6$ are each independently selected from H, $C_{1-4}$alkyl, $C_{1-4}$ alkoxy, $C_{1-4}$ haloalkyl, $C_{1-4}$ haloalkoxy, halogen, OH, CN and $NH_2$, wherein the $C_{1-4}$ alkyl, $C_{1-4}$ alkoxy, $C_{1-4}$haloalkyl or $C_{1-4}$haloalkoxy of $R^5$ and $R^6$ are each further optionally substituted with from 1-2 members independently selected from halo, OH, CN, $NH_2$, $OR^7$, $NHR^7$, $NR^7R^7$, $C_{1-4}$ alkyl, $C_{1-4}$alkoxy, $C_{1-4}$ haloalkyl, and $C_{1-4}$ haloalkoxy, wherein each $R^7$ is independently $C_{1-4}$ alkyl; or $R^5$ and $R^6$ taken together with the carbon atom to which they are attached form a $C_{3-6}$ cycloalkyl ring, optionally substituted with OH, CN, $NH_2$, $OR^7$, $NHR^7$, $NHR^7$, $C_{1-4}$ alkyl, $C_{1-4}$ alkoxy, $C_{1-4}$haloalkyl or $C_{1-4}$ haloalkoxy; and m is 1, 2 or 3.

In some embodiments of compounds of Formula (I), L is a bond or —$(CR^5R^6)_m$—. In one instance, L is a bond. In another instance, L is —$(CR^5R^6)_m$—. In another instance, L is —$(CH_2)_m$—, where m is 1, 2 or 3. In certain embodiments, L is —$(CR^5R^6)_m$—, where $R^5$ and $R^6$ taken together with the carbon atom to which they are attached form a $C_{3-6}$ cycloalkyl ring, optionally substituted with OH, CN, $NH_2$, $OR^7$, $NHR^7$, $NHR^7$, $C_{1-4}$ alkyl, $C_{1-4}$ alkoxy, $C_{1-4}$ haloalkyl or $C_{1-4}$haloalkox. In certain instances, L is —$(CR^5R^6)_m$—, where $R^5$ and $R^6$ taken together with the carbon atom to which they are attached form a cyclopropyl, cyclobutyl, cyclopentyl or cyclohexyl ring, each of which is optionally substituted with from 1-2 members independently selected from OH, CN, $NH_2$, $OR^7$, $NHR^7$, $NHR^7$, $C_{1-4}$ alkyl, $C_{1-4}$ alkoxy, $C_{1-4}$ haloalkyl, and $C_{1-4}$haloalkox.

In some embodiments of compounds of Formula (I), X is a bond, —C(O)— or —$CR^8R^9$—, wherein $R^8$ and $R^9$ are each independently H, $C_{1-4}$ alkyl, $C_{1-4}$ alkoxy, $C_{1-4}$ haloalkyl or $C_{1-4}$haloalkoxy, wherein the $C_{1-4}$ alkyl, $C_{1-4}$ alkoxy, $C_{1-4}$ haloalkyl and $C_{1-4}$ haloalkoxy of $R^8$ and $R^9$ are each optionally substituted with 1-2 members independently selected from OH, CN, $NH_2$, $OR^7$, $NHR^7$, $NHR^7$, $C_{1-4}$ alkyl, $C_{1-4}$ alkoxy, $C_{1-4}$ haloalkyl or $C_{1-4}$ haloalkoxy; or $R^8$ and $R^9$ taken together with the carbon atom to which they are attached form a $C_{3-6}$ cycloalkyl ring, optionally substituted with from 1-2 members independently selected from OH, CN, $NH_2$, $OR^7$, $NHR^7$, $NHR^7$, $C_{1-4}$alkyl, $C_{1-4}$ alkoxy, $C_{1-4}$ haloalkyl and $C_{1-4}$ haloalkoxy.

In some embodiments of compounds of Formula (I), X is a bond.

In some embodiments of compounds of Formula (I), X is —C(O) or —$CR^8R^9$—, wherein $R^8$ and $R^9$ are each independently H, $C_{1-4}$ alkyl, $C_{1-4}$ alkoxy, $C_{1-4}$haloalkyl or $C_{1-4}$haloalkoxy, wherein the $C_{1-4}$ alkyl, $C_{1-4}$ alkoxy, $C_{1-4}$ haloalkyl and $C_{1-4}$ haloalkoxy of $R^8$ and $R^9$ are each optionally substituted with 1-2 members independently selected from OH, CN, $NH_2$, $OR^7$, $NHR^7$, $NHR^7$, $C_{1-4}$ alkyl, $C_{1-4}$ alkoxy, $C_{1-4}$ haloalkyl, and $C_{1-4}$ haloalkoxy. In some instances, X is —C(O)— or —$CH_2$—. In other instances, X is —$CR^8R^9$—, where $R^8$ and $R^9$ taken together with the carbon atom to which they are attached form a $C_{3-6}$ cycloalkyl ring, optionally substituted with from 1-2 members independently selected from OH, CN, $NH_2$, $OR^7$, $NHR^7$, $NHR^7$, $C_{1-4}$ alkyl, $C_{1-4}$ alkoxy, $C_{1-4}$ haloalkyl, and $C_{1-4}$ haloalkoxy. In certain instances, X is —$CR^8R^9$—, where $R^8$ and $R^9$ taken together with the carbon atom to which they are attached form cyclopropyl, cyclobutyl, cclopentyl, or cyclohexyl ring, each of which is optionally substituted with from 1-2 members independently selected from OH, CN, $NH_2$, $OR^7$, $NHR^7$, $NR^7R^7$, $C_{1-4}$ alkyl, $C_{1-4}$ alkoxy, $C_{1-4}$ haloalkyl, and $C_{1-4}$ haloalkoxy.

In some embodiments of compounds of Formula (I), $R^1$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^a\text{-}C(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^1$ are each optionally substituted with 1, 2, 3, or 4 $R^b$ substituents independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^c$, $SR^c$, $C(O)R^c$, $C(O)NR^cR^c$, $C(O)OR^c$, $OC(O)R^c$, $OC(O)NR^cR^c$, $C(=NR^c)$ $NR^cR^c$, $NR^cC(=NR^c)NR^cR^c$, $NR^cR^c$, $NR^c(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with from 1-3 $R^d$ substituents.

In some embodiments of compounds of Formula (I), $R^1$ is $C_{1-6}$ alkyl, 5 to 6-membered heteroaryl, 4 to 7-membered heterocycloalkyl-$C_{1-4}$ alkyl, or $C_{6-10}$ aryl, each of which is optionally substituted with from 1-3 independently selected $R^b$ groups.

In some embodiments of compounds of Formula (I), $R^1$ is $C_{1-6}$ alkyl, 5 or 6-membered heteroaryl, or phenyl, each of which is substituted with from 1-3 independently selected $R^b$ groups.

In some embodiments of the compounds of Formula (I):
each $R^1$ is independently selected from $C_{1-6}$ alkyl, $C_{1-6}$ haloalkyl, $C_{6-10}$ aryl-$C_{1-4}$ alkyl-, $C_{3-10}$cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, each of which is optionally substituted with 1-2 $R^b$ substituents;

each $R^b$ is independently selected from $C_{1-6}$ alkyl, $C_{1-4}$ haloalkyl, halo, CN, $NHOR^c$, $OR^c$, $C(O)NR^cR^c$, $C(O)OR^c$, $OC(O)R^c$, $OC(O)NR^cR^c$, $NR^cR^c$, $NR^cR^c$, $NR^cC(O)R^c$, $NR^c\text{-}C(O)OR^c$, $NR^cC(O)NR^cR^c$, $NR^cS(O)_2R^c$, $NR^cS(O)_2NR^cR^c$, $S(O)_2R^c$, and $S(O)_2NR^cR^c$;

each $R^c$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1-2 $R^f$ substituents; and each $R^f$ substituents independently selected from F, Cl, OH, $C_{1-4}$ alkoxy, $C_{1-4}$ haloalkoxy, $NH_2$, $NH(C_{1-4}$ alkyl), $N(C_{1-4}$ alkyl$)_2$, $C(O)(C_{1-4}$ alkyl), $C(O)NH_2$, $C(O)NH(C_{1-4}$ alkyl), $C(O)N(C_{1-4}$ alkyl$)_2$, $NHC(O)NH_2$, $NHC(O)NH(C_{1-4}$ alkyl), $NHC(O) N(C_{1-4}$ alkyl$)_2$, $OC(O)(C_{1-4}$ alkyl), $NHC(O)(C_{1-4}$ alkyl), $NHS(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl$)_2$, $NHS(O)_2NH_2$, $NHS(O)_2NH(C_{1-4}$ alkyl), and $NHS(O)_2N(C_{1-4}$ alkyl$)_2$.

In some embodiments of the compounds of Formula (I):
each $R^b$ is independently selected from halo, $NR^cR^c$, and $C_{1-6}$ alkyl; and
each $R^c$ is independently selected from $C_{1-6}$ alkyl, $C_{3-6}$ cycloalkyl, and 4-6 membered heterocycloalkyl; wherein said $C_{1-6}$ alkyl of $R^c$ is optionally substituted with OH.

In some embodiments of the compounds of Formula (I), $R^1$ is morpholinylmethyl, cyclohexylaminomethyl, cyclopenylaminomethyl, 4-tetrahydro-2H-pyranylaminomethyl, $C_{1-4}$alkylamino-$C_{1-4}$alkyl, pyrazolyl, imidazolyl, 2-hydroxyethylaminomethyl or phenyl, each of which is optionally substituted with 1-3 members independently selected from OH, CN, amino, halo, $C_{1-4}$ alkyl, $C_{1-4}$ alkoxy, $C_{1-4}$ alkylthio, $NH_2$, $NH(C_{1-4}$ alkyl), $NH(C_{1-4}$ alkyl$)_2$, $C_{1-4}$ haloalkyl, and $C_{1-4}$ haloalkoxy.

In some embodiments of the compounds of Formula (I), $R^1$ is morpholin-4-ylmethyl, 2-hydroxyethylaminomethyl, cyclopentylaminomethyl, cyclohexylaminomethyl, tetrahydro-2H-pyran-4-yl-aminomethyl, 1-methylimidazol-4-yl, or 2,6-difluorophenyl.

In some embodiments of the compounds of Formula (I), $R^1$ is morpholinylmethyl, cyclohexylaminomethyl, cyclopenylaminomethyl, 4-tetrahydro-2H-pyranylaminomethyl, $C_{1-4}$alkylamino-$C_{1-4}$alkyl, $C_{3-6}$cycloalkylamino-$C_{1-4}$alkyl, 4 to 10-membered heterocycloalkylamino-$C_{1-4}$alkyl, pyrazolyl, imidazolyl, 2-hydroxyethylaminomethyl or phenyl, each of which is optionally substituted with 1-3 members independently selected from OH, CN, amino, halo, $C_{1-4}$ alkyl, $C_{1-4}$ alkoxy, $C_{1-4}$ alkylthio, $NHR^7$, $NR^7R^7$, $C_{1-4}$ haloalkyl, and $C_{1-4}$ haloalkoxy.

In some embodiments of the compounds of Formula (I), $R^1$ is morpholinylmethyl, cyclohexylaminomethyl, 4-tetrahydro-2H-pyranylaminomethyl, 2-hydroxyethylaminomethyl, cyclopentylaminomethyl, phenyl, imdidazolyl, or pyrazolyl, each of which is optionally substituted with from 1-3 members independently selected from OH, CN, amino, halo, $C_{1-4}$ alkyl, $C_{1-4}$ alkoxy, $C_{1-4}$ alkylthio, $NH_2$, $NHR^7$, $NR^7R^7$, $C_{1-4}$ haloalkyl, and $C_{1-4}$ haloalkoxy.

In some embodiments of compounds of Formula (I), $R^2$ is $C_{1-6}$alkyl optionally substituted with from 1-3 $R^b$ groups. In some instances, $R^2$ is $C_{1-6}$alkyl. In one instance, $R^2$ is butyl. In another instance, $R^2$ is n-butyl.

In some embodiments of compounds of Formula (I), $R^3$ is H or $C_{1-6}$alkyl. In one instance, $R^3$ is H.

In some embodiments of compounds of Formula (I), $R^4$ is $-NH_2$, $-NHOH$, $-OH$, $-CN$, $-COOH$, $C_{1-4}$ alkyl, $C_{1-4}$ alkoxy, $C_{1-2}$ haloalkyl, $C_{1-2}$ haloalkoxy, $-N(R^{10})_2$, $NHOR^{10}$, $-NHC(O)R^{10}$, $-C(O)R^{10}$, $-C(O)NR^{10}R^{10}$, $-C(O)OR^{10}$, $-OC(O)R^{10}$, $-OC(O)NR^{10}R^{10}$, $-NR^{10}R^{10}$, $-NR^{10}C(O)OR^{10}$, $-NR^{10}C(O)OR^{10}$, wherein each $R^{10}$ is independently $C_{1-4}$alkyl, $C_{6-10}$ aryl, and $C_{1-2}$-haloalkyl each of which is optionally substituted with 1-2 independently selected $R^f$ groups; wherein $C_{1-4}$ alkyl, $C_{1-4}$ alkoxy, $C_{1-2}$ haloalkyl and $C_{1-2}$ haloalkoxy of $R^4$ are each optionally substituted with from 1-3 $R^m$ substituents independently selected from OH, CN, amino, halo, $C_{1-4}$ alkyl, $C_{1-4}$ alkoxy, $C_{1-4}$ alkylthio, $NHR^7$, $NR^7R^7$, $C_{1-4}$ haloalkyl, and $C_{1-4}$ haloalkoxy. In certain instances, $R^4$ is $-NH_2$, $-NHOH$, $-OH$, $-CN$, $-COOH$, $C_{1-4}$ alkyl, $C_{1-4}$ alkoxy, $C_{1-2}$ haloalkyl, $C_{1-2}$ haloalkoxy, $-NHR^{10}$, $-N(R^{10})_2$, or $NHOR^{10}$, where $R^{10}$ is $C_{1-4}$ alkyl. In some instances, $R^4$ is $-NH_2$, $-NHOH$, $-OH$, $-CN$, $-COOH$, $-CH_3$, —OCH$_3$, CF$_3$, —OCF$_3$, —NHCH$_3$, or —N(CH$_3$)$_2$. In one embodiment, R$^4$ is NH$_2$, OH, or NHOH. In another embodiment, R$^4$ is NH$_2$ or OH.

In some embodiments of the compounds of Formula (I), n is 1.

In some embodiments of compounds of Formula (I), the two substituents on ring B are in trans configuration with respect to each other, when ring B is C$_{3-6}$ cycloalkyl or 4 to 10-membered heterocycloalkyl. For example, the substituent R$^4$ and moiety

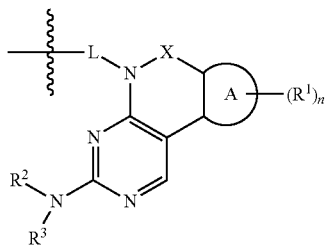

attached to ring B are in trans configuration with respect to each other.

In some embodiments of the compounds of Formula (I):
A is fused phenyl;
B is C$_{3-6}$ cycloalkyl or 4- to 6-membered heterocycloalkyl;
X is CH$_2$ or C(O);
L is a bond;
each R$^1$ is C$_{1-6}$ alkyl, C$_{1-6}$ haloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, each of which is optionally substituted with 1-2 R$^b$ substituents;
each R$^b$ is independently selected from C$_{1-6}$ alkyl, C$_{1-4}$ haloalkyl, halo, CN, NHOR$^c$, OR$^c$, C(O)NR$^c$R$^c$, C(O)OR$^c$, OC(O)R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, NR$^c$S(O)$_2$R$^c$, NR$^c$S(O)$_2$NR$^c$R$^c$, S(O)$_2$R$^c$, and S(O)$_2$NR$^c$R$^c$;
each R$^c$ is independently selected from C$_{1-6}$ alkyl, C$_{1-4}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^c$ are each optionally substituted with 1-2 R$^f$ substituents;
each R$^f$ substituent is independently selected from F, Cl, OH, C$_{1-4}$ alkoxy, C$_{1-4}$ haloalkoxy, NH$_2$, NH(C$_{1-4}$ alkyl), N(C$_{1-4}$ alkyl)$_2$, C(O)(C$_{1-4}$ alkyl), C(O)NH$_2$, C(O)NH—C$_{1-4}$ alkyl, C(O)N(C$_{1-4}$ alkyl)$_2$, NHC(O)NH$_2$, NHC(O)NH(C$_{1-4}$ alkyl), NHC(O)N(C$_{1-4}$ alkyl)$_2$, OC(O)—C$_{1-4}$ alkyl, NHC(O)—C$_{1-4}$ alkyl, NHS(O)$_2$—C$_{1-4}$ alkyl, S(O)$_2$—C$_{1-4}$ alkyl, S(O)$_2$NH$_2$, S(O)$_2$NH—C$_{1-4}$ alkyl, S(O)$_2$N(C$_{1-4}$ alkyl)$_2$, NHS(O)$_2$NH$_2$, NHS(O)$_2$NH—C$_{1-4}$ alkyl, and NHS(O)$_2$N(C$_{1-4}$ alkyl)$_2$;
R$^2$ is C$_{1-6}$ alkyl;
R$^3$ is H or C$_{1-4}$ alkyl;
R$^4$ is NH$_2$, NH(C$_{1-4}$ alkyl), N(C$_{1-4}$ alkyl)$_2$, OH, or O(C$_{1-4}$ alkyl); and
n is 1.

In some embodiments of the compounds of Formula (I):
A is fused phenyl;
B is cyclopropyl, cyclobutyl, cyclopentyl, or cyclohexyl;
X is CH$_2$ or C(O);
L is a bond;
each R$^1$ is C$_{1-6}$ alkyl, C$_{1-6}$ haloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, or (4-10 membered heterocycloalkyl)-C$_{1-4}$ alkyl-, each optionally substituted with 1-2 R$^b$ substituents;
each R$^b$ is independently selected from C$_{1-6}$ alkyl, C$_{1-4}$ haloalkyl, halo, CN, NHOR$^c$, OR$^c$, C(O)NR$^c$R$^c$, C(O)OR$^c$, OC(O)R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, NR$^c$S(O)$_2$R$^c$, NR$^c$S(O)$_2$NR$^c$R$^c$, S(O)$_2$R$^c$, and S(O)$_2$NR$^c$R$^c$;
each R$^c$ is independently selected from C$_{1-6}$ alkyl, C$_{1-4}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^c$ are each optionally substituted with 1-2 R$^f$ substituents;
each R$^f$ substituents independently selected from F, Cl, OH, C$_{1-4}$ alkoxy, C$_{1-4}$ haloalkoxy, NH$_2$, NH(C$_{1-4}$ alkyl), N(C$_{1-4}$ alkyl)$_2$, C(O)(C$_{1-4}$ alkyl), C(O)NH$_2$, C(O)NH—C$_{1-4}$ alkyl, C(O)N(C$_{1-4}$ alkyl)$_2$, NHC(O)NH$_2$, NHC(O)NH(C$_{1-4}$ alkyl), NHC(O)N(C$_{1-4}$ alkyl)$_2$, OC(O)—C$_{1-4}$ alkyl, NHC(O)—C$_{1-4}$ alkyl, NHS(O)$_2$—C$_{1-4}$ alkyl, S(O)$_2$—C$_{1-4}$ alkyl, S(O)$_2$NH$_2$, S(O)$_2$NH—C$_{1-4}$ alkyl, S(O)$_2$N(C$_{1-4}$ alkyl)$_2$, NHS(O)$_2$NH$_2$, NHS(O)$_2$NH—C$_{1-4}$ alkyl, and NHS(O)$_2$N(C$_{1-4}$ alkyl)$_2$;
R$^2$ is C$_{1-6}$ alkyl;
R$^3$ is H or C$_{1-4}$ alkyl;
R$^4$ is NH$_2$, NH(C$_{1-4}$ alkyl), N(C$_{1-4}$ alkyl)$_2$, OH, or O(C$_{1-4}$ alkyl); and
n is 1.

In some embodiments of the compounds of Formula (I):
A is fused phenyl;
B is cyclohexyl;
X is CH$_2$ or C(O);
L is a bond;
R$^1$ is C$_{1-6}$alkyl, 5 to 6-membered heteroaryl, 4 to 7-membered heterocycloalkyl-C$_{1-4}$alkyl or C$_{6-10}$ aryl, each of which is optionally substituted with from 1-3 independently selected R$^b$ groups;
each R$^b$ is independently selected from halo, NR$^c$R$^c$, and C$_{1-6}$ alkyl;
each R$^c$ is independently selected from C$_{1-6}$ alkyl, C$_{3-6}$ cycloalkyl, and 4-6 membered heterocycloalkyl; wherein said C$_{1-6}$ alkyl of R$^c$ is optionally substituted with 1 R$^f$ substituent independently selected from OH;
R$^2$ is C$_{1-6}$ alkyl;
R$^3$ is H or C$_{1-4}$ alkyl;
R$^4$ is NH$_2$ or OH; and
n is 1.

In some embodiments, the compound is a compound of Formula (V):

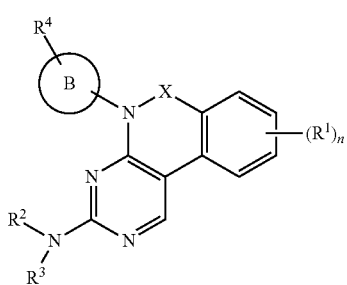

or a pharmaceutically acceptable salt thereof.

Subformulas

In some embodiments, compounds of Formula (I) have subformula (II):

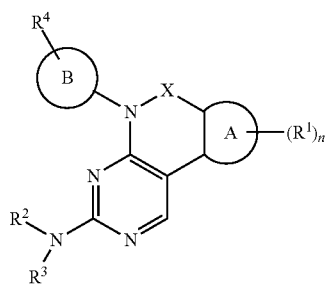

or a pharmaceutically acceptable salt thereof, wherein the variables ring A, ring B, $R^1$, $R^2$, $R^3$, $R^4$, X and n are as defined in any embodiment of compounds of Formula (I). In some embodiments, X is —$CH_2$— or —C(O)—. In other embodiments, $R^4$ is $NH_2$ or OH. In one embodiment, ring A is fused phenyl. In other embodiments, ring B is $C_{3-6}$cycloalkyl. In other embodiments, $R^2$ is $C_{1-6}$alkyl and $R^3$ is H.

In some embodiments, compounds of Formula (I) have subformula (III):

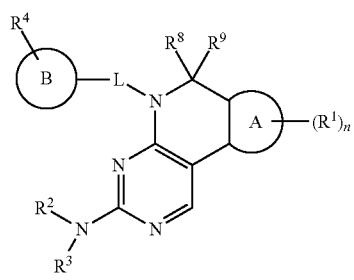

or a pharmaceutically acceptable salt, a tautomer or an isomer thereof, wherein the variables ring A, ring B, $R^1$, $R^2$, $R^3$, $R^4$, $R^8$, $R^9$, L and n are as defined in any embodiment of compounds of Formula (I). In one embodiment, $R^8$ and $R^9$ are H. In another embodiment, $R^8$ and $R^9$ taken together with the carbon atom to which they are attached form a cyclopropyl ring, optionally substituted with from 1-2 members selected from OH, CN, $NH_2$, $OR^7$, $NHR^7$, $NR^7R^7$, $C_{1-4}$alkyl, $C_{1-4}$ alkoxy, $C_{1-4}$ haloalkyl and $C_{1-4}$ haloalkoxy. In one embodiment, L is a bond. In some embodiments, $R^4$ is $NH_2$ or OH. In one embodiment, ring A is fused phenyl. In other embodiments, ring B is $C_{3-6}$ cycloalkyl. In other embodiments, $R^2$ is $C_{1-6}$alkyl and $R^3$ is H.

In some embodiments, compounds of Formula (I) have subformula (IV):

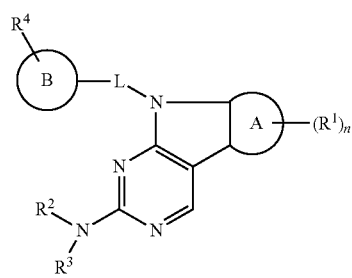

or a pharmaceutically acceptable salt, a tautomer or an isomer thereof, wherein the variables ring A, ring B, $R^1$, $R^2$, $R^3$, $R^4$, L and n are as defined in any embodiment of compounds of Formula (I). In one embodiment, L is a bond. In some embodiments, $R^4$ is $NH_2$ or OH. In one embodiment, ring A is fused phenyl. In other embodiments, ring B is $C_{3-6}$cycloalkyl. In other embodiments, $R^2$ is $C_{1-6}$alkyl and $R^3$ is H.

In some embodiments, compounds of Formula (I) have subformula (Va):

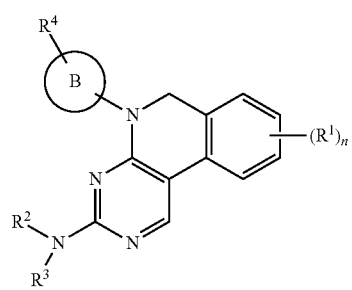

or a pharmaceutically acceptable salt, a tautomer or an isomer thereof.

In some embodiments, compounds of Formula (I) have subformula (Vb):

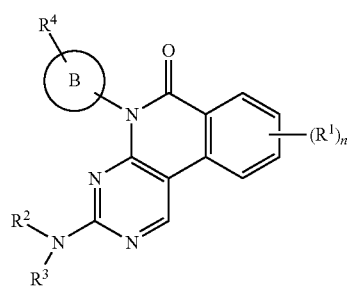

or a pharmaceutically acceptable salt, a tautomer or an isomer thereof.

In some embodiments, compounds of Formula (I) have subformula (VI):

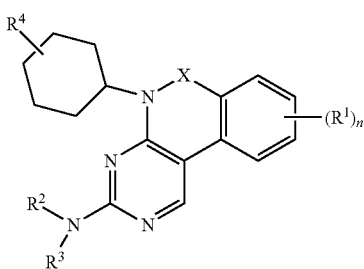

(VI)

or a pharmaceutically acceptable salt, a tautomer or an isomer thereof.

In some embodiments, compounds of Formula (I) have subformula (VIa):

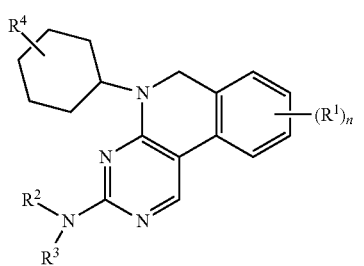

(VIa)

or a pharmaceutically acceptable salt, a tautomer or an isomer thereof.

In some embodiments, compounds of Formula (I) have subformula (VIb):

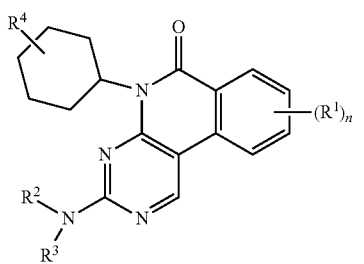

(VIb)

or a pharmaceutically acceptable salt, a tautomer or an isomer thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub combination.

Definitions

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$" where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ or a $C_{3-6}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, 4 to 7 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In certain embodiments, the heterocyloalkyl group is a monocyclic or bicyclic non-aromatic ring or ring system having 4 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring. In another preferred embodiment, the heterocyloalkyl group is a monocyclic non-aromatic ring or ring system having 4 to 7 ring-forming atoms, wherein 1 to 3 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring.

As used herein, the term "aryl" employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "heteroaryl," employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In certain embodiments, the heteroaryl group is a monocyclic or bicyclic aromatic ring system having 5 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl. In another preferred embodiment, the heteroaryl group is a monocyclic aromatic ring system having 5 to 6 ring-forming atoms, wherein 1 to 4 ring-forming atoms are heteroatoms independently selected from N, O, and S, wherein the N and S as ring members are each optionally oxidized, the carbon ring members may be optionally replaced by carbonyl.

When two alkyl groups are shown attached to a nitrogen atom on a substituent group (e.g., $N(C_{1-4}$ alkyl$)_2$), it is intended that each alkyl group be selected independently from the other. For example, each group can be different (e.g., one alkyl group can be methyl and the other ethyl); alternatively, both groups can be the same (e.g., ethyl).

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. The term "isomer", as used herein, refers to a stereoisomer of the compound, such as an enantiomer, racemate, rotamer, conformer, diastereomer, or optical isomer of the compound.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TAM kinases with a compound of the invention includes the administration of a compound of the present invention to an individual or patient, such as a human, having TAM, as well as, for example, introducing a compound of the invention into a sample containing a cellular or purified preparation containing the TAM kinases.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature. Example synthetic methods for preparing compounds of the invention are provided in the Schemes below.

A series of tricyclic compounds of formula 9 and 10 can be prepared by the methods outlined in Scheme 1. Amino pyrimidine 2 can be synthesized by a chemo-selective displacement of 4-Cl in 2, 4-dichloro-5-bromopyrimidine 1 with suitable 4-substituted cyclohexylamines. The resulting 2-chloropyrimidine 2 was subjected to another nucleophilic substitution by a variety of amines, which includes, but not limited to, methylamine, ethylamine, butylamine, etc. The tricyclic lactam 5 was formed by a cascade sequence featuring a Suzuki coupling of bromo 3 and boronic ester 4, in situ hydrolysis of cyano to amide and the subsequent ring closure. Compounds of formula 10 can be accessed from tricyclic chloride 5 by palladium or copper catalyzed C—C, C—N and C—O bond formation which includes, but not limited to, Suzuki coupling, Stille coupling, Neigishi coupling, Sonogashira coupling, Buchwald coupling, Hartwig coupling, etc. The compounds as disclosed herein or compounds as recited in the claims can be prepared readily in accordance with the synthetic proctocols set forth in Schemes 1-3.

osmium tetraoxide/sodium periodate. The reductive amination of aldehyde 7 with a variety of amines includes, but not limit to, dimethylamine, morpholine, cyclohexylamine, cyclopentanamine, etc. afford the benzylic amine 8. The reduction of lactam 8 required strong reducing agents such as lithium aluminum hydride or borane complex. In the case of $R^4$ is a substituted amino group, a deprotection reaction was required to reveal the amine.

An alternative synthetic route from bromopyrimidine 3 to tricyclic amine 9 was outlined in Scheme 2. A different boronic ester 11 was used in the Suzuki coupling to form the alcohol 12 as a result of in situ hydrolysis of the benzyl bromide. The key cyclization of alcohol 12 to tricyclic amine 13 can be achieved by an oxidation/reduction sequence. The oxidant includes, but not limit to, Dess-Martin Periodinane, $MnO_2$, TEMPO oxidation, Swern Oxidation, etc; the reducing agents includes, but not limit to,

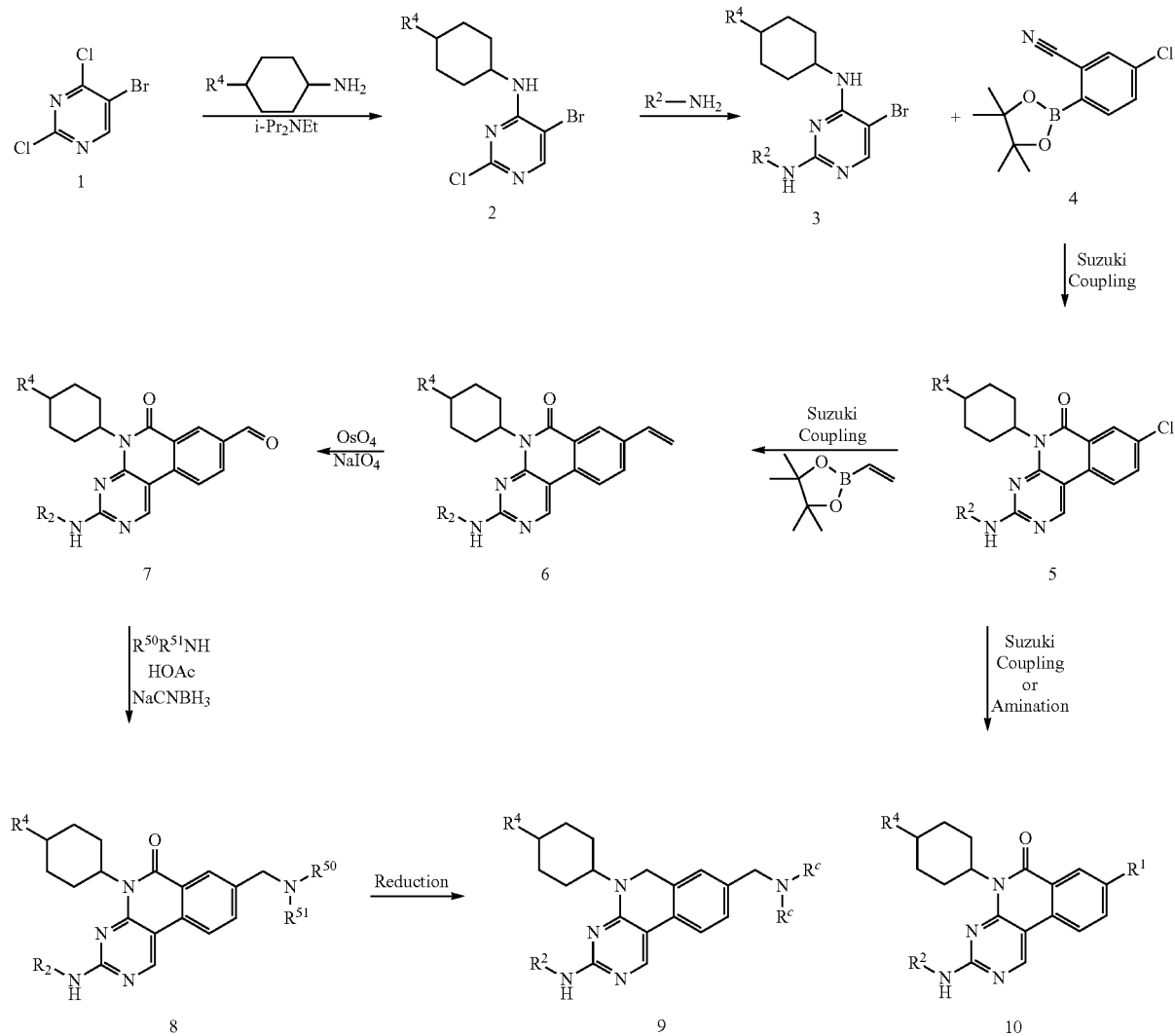

Scheme 1

To synthesize compounds of formula 9, aryl chloride 5 can be converted to aldehyde 7 by a Suzuki coupling to vinyl boronic ester and then oxidative cleavage of olefin 6 by $NaCNBH_3$, $NaBH_4$, $NaBH(OAc)_3$, etc. The synthesis of compound 9 from aryl chloride 13 was similar as outlined in Scheme 1.

Scheme 2

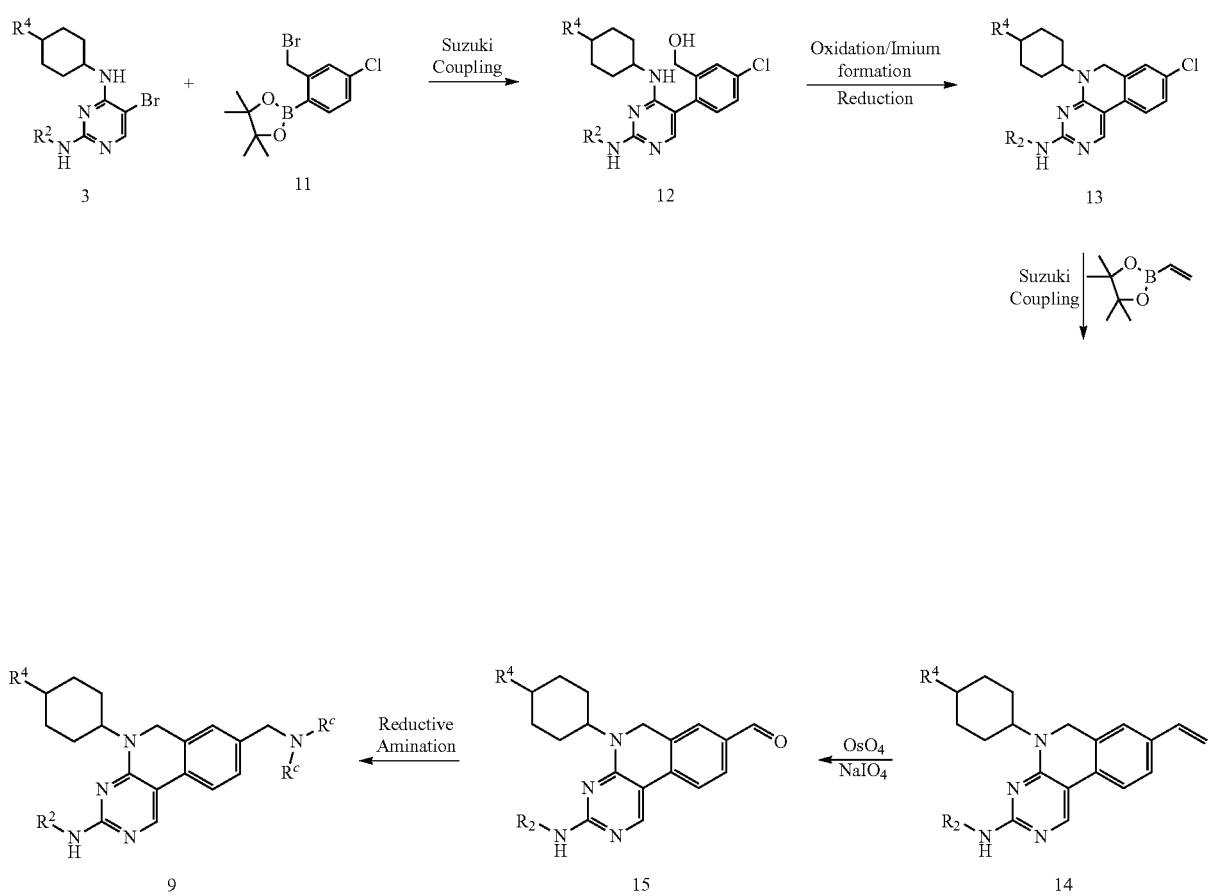

Other compounds of Formula (I) can be formed as shown in Scheme 3. Amino pyrimidine b can be synthesized by a chemo-selective displacement of 4-Cl in 2,4-dichloro-5-bromopyrimidine a with suitable amines. The resulting pyrimidine b can be subjected to another nucleophilic substitution by an amine of formula $R^2$—$NH_2$ to form compound c. The tricyclic lactam e can be formed by a cascade sequence featuring a Suzuki coupling of bromo c and boronic ester d, in situ hydrolysis of cyano to amide, and the subsequent ring closure. Compounds of formula j can be accessed from tricyclic chloride e by palladium or copper catalyzed C—C, C—N and C—O bond formation which includes, but not limited to, Suzuki coupling, Stille coupling, Neigishi coupling, Sonogashira coupling, Buchwald coupling, Hartwig coupling, etc. To synthesize compounds of formula i, aryl chloride e can be converted to aldehyde g by a Suzuki coupling to vinyl boronic ester and then oxidative cleavage of olefin f by osmium tetraoxide/sodium periodate. The reductive amination of aldehyde g with a variety of amines includes, but not limit to, dimethylamine, morpholine, cyclohexylamine, cyclopentanamine, etc. afford the benzylic amine h. The reduction of lactam h can be accomplished by use of strong reducing agents such as lithium aluminum hydride or borane complex.

Scheme 3

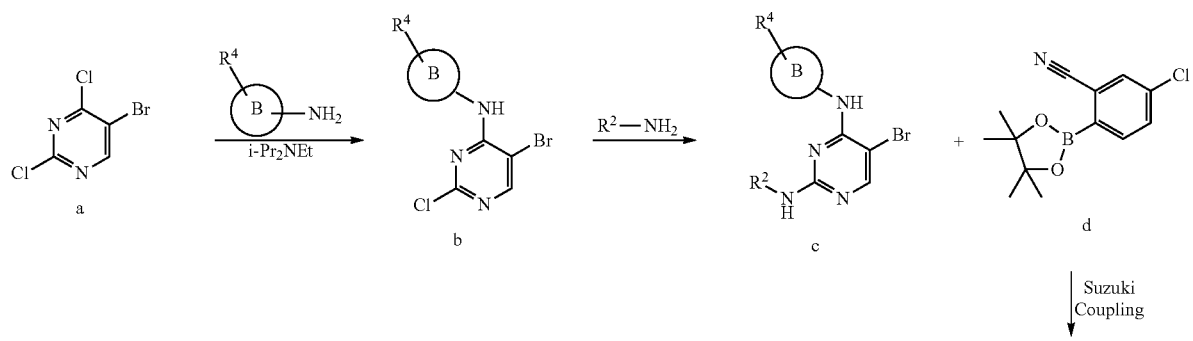

-continued

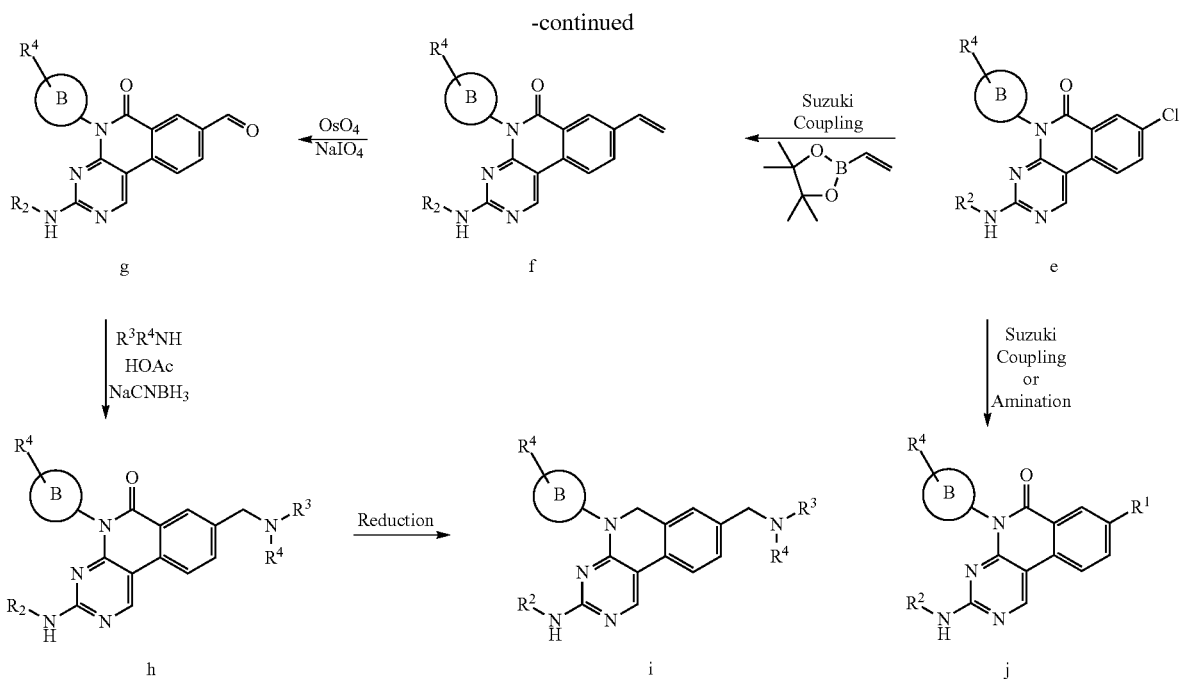

TAM Kinases

Receptor tyrosine kinases (RTKs) are cell surface proteins that transmit signals from the extracellular environment to the cell cytoplasm and nucleus to regulate cellular events such as survival, growth, proliferation, differentiation, adhesion and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity. The TAM subfamily consists of three RTKs including TYRO3, AXL and MER (Graham et al., 2014, Nature reviews Cancer 14, 769-785; and Linger et al., 2008, Oncogene 32, 3420-3431). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are over-expressed in many cancers and play important roles in tumor initiation and maintenance; therefore, TAM inhibition represents an attractive approach for targeting another class of oncogenic RTKs (Graham et al., 2014, Nature reviews Cancer 14, 769-785; and Linger et al., 2008, Oncogene 32, 3420-3431).

Axl was originally identified as a transforming gene from DNA of patients with chronic myelogenous leukemia (O'Bryan et al., 1991, Molecular and cellular biology 11, 5016-5031). GAS6 binds to Axl and induces subsequent auto-phosphorylation and activation of Axl tyrosine kinase. Axl activates several downstream signaling pathways including PI3K-Akt, Raf-MAPK, PLC-PKC (Feneyrolles et al., 2014, Molecular cancer therapeutics 13, 2141-2148; Linger et al., 2008, Oncogene 32, 3420-3431). AXL is over-expressed or amplified in a variety of malignancies including lung cancer, prostate cancer, colon cancer, breast cancer, melanoma, and renal cell carcinoma (Linger et al., 2008, Oncogene 32, 3420-3431). Over-expression of AXL is correlated with poor prognosis (Linger et al., 2008, Oncogene 32, 3420-3431). As a result, AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer biology & therapy 8, 618-626). In prostate cancer, AXL inhibition decreased cell migration, invasion, and proliferation (Tai et al., 2008, Oncogene 27, 4044-4055). In addition, AXL over-expression or amplification is a major mechanism for resistance to EGFR inhibitors by lung cancer cells, and AXL inhibition can reverse the resistance (Zhang et al., 2012, Nature genetics 44, 852-860).

Mer was originally identified as a phospho-protein from a lymphoblastoid expression library (Graham et al., 1995, Oncogene 10, 2349-2359). Both GAS6 and ProS can bind to Mer and induce the phosphorylation and activation of Mer kinase (Lew et al., 2014. eLife, 3:e03385). Like Axl, Mer activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

Tyro3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

In addition to their role as transforming oncogenes, TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

TAM kinases have been shown to function as checkpoints for immune activation in the tumor milieu. All TAM kinases are expressed in NK cells, and TAM kinases inhibit the anti-tumor activity of NK cells. LDC1267, a small molecule TAM inhibitor, activates NK cells, and blocks metastasis in tumor models with different histologies (Paolino et al., 2014, Nature 507, 508-512). In addition, MER kinase promotes the activity of tumor associated macrophages through the increased secretion of immune suppressive cytokines such as IL10 and IL4, and decreased production of immune activating cytokines such as IL12 (Cook et al., 2013, The Journal of clinical investigation 123, 3231-3242). MER inhibition has been shown to reverse this effect. As a result, MER knockout mice are resistant to PyVmT tumor formation (Cook et al., 2013, The Journal of clinical investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks after birth (Chambers et al., 1997, Immunity 7, 885-895; and Nishimura et al., 2001, Science 291, 319-322).

TAM inhibition will have not only direct activity against neoplastic cells, but also activate the anti-cancer immune response. Thus TAM inhibitors represent an attractive approach for the treatment of cancer as single agents. In addition, TAM inhibitors may be combined with other targeted therapies, chemotherapies, radiation, or immunotherapeutic agents to achieve maximal efficacy in the clinic.

Methods of Use

Compounds of the present disclosure can modulate or inhibit the activity of TAM kinases. For example, the compounds of the disclosure can be used to inhibit activity of a TAM kinase in a cell or in an individual or patient in need of inhibition of the kinases by administering an inhibiting amount of a compound of the disclosure to the cell, individual, or patient.

In some embodiments, the compounds of the disclosure are selective for the TAM kinases over one or more of other kinases. In some embodiments, the compounds of the disclosure are selective for the TAM kinases over other kinases. In some embodiments, the selectivity is 2-fold or more, 3-fold or more, 5-fold or more, 10-fold or more, 25-fold or more, 50-fold or more, or 100-fold or more.

As TAM kinases inhibitors, the compounds of the disclosure are useful in the treatment of various diseases associated with abnormal expression or activity of the TAM kinases. Compounds which inhibit TAM kinases will be useful in providing a means of preventing the growth or inducing apoptosis in tumors, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors.

In certain embodiments, the disclosure provides a method for treating a disease or disorder mediated by TAM kinases in a patient in need thereof, comprising the step of administering to said patient a compound according to the invention, or a pharmaceutically acceptable composition thereof.

For example, the compounds of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Compounds of the disclosure can also be useful in the inhibition of tumor metastisis.

In some embodiments, the present disclosure provides a method for treating hepatocellular carcinoma in a patient in need thereof, comprising the step of administering to said patient a compound of Formula (I) or a compound as disclosed herein, or a pharmaceutically acceptable salt thereof, or a composition comprising a compound of Formula (I) or a compound as disclosed herein.

In some embodiments, the present disclosure provides a method for treating Rhabdomyo sarcoma, esophageal cancer, breast cancer, or cancer of a head or neck, in a patient in need thereof, comprising the step of administering to said patient a compound Formula (I) or a compound as disclosed herein, or a pharmaceutically acceptable salt thereof, or a composition comprising a compound of Formula (I) or a compound as disclosed herein.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of Formula (I) or a compound as described herein for treatment of TAM-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methyl ethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds of the present application for the treatment of cancer include chemotherapeutic agents, targeted cancer therapies, immunotherapies or radiation therapy. Compounds of this application may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present disclosure. These include anti-androgens including but not limited to flutamide, bicalutamide, and nilutamide, luteinizing hormone-releasing hormone (LHRH) analogs including leuprolide, oserelin, triptorelin, and histrelin, LHRH antagonists (e.g. degarelix), androgen receptor blockers (e.g. enzalutamide) and agents that inhibit androgen production (e.g. abiraterone).

Compounds of the present disclosure may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with TAM inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib. Agents against FGFRs include but are not limited to AZD4547, BAY1187982, ARQ087, BGJ398, BIBF1120, TKI258, lucitanib, dovitinib, TAS-120, JNJ-42756493, and Debio1347. Agents against Trks include but are not limited to LOXO-101, and RXDX-101.

Angiogenesis inhibitors may be efficacious in some tumors in combination with TAM inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present disclosure include inhibitors of the PI3K-AKT-mTOR pathway, inhibitors of the Raf-MAPK pathway, inhibitors of PIM kinases, inhibitors of JAK-STAT pathway, and inhibitors of protein chaperones and cell cycle progression.

Agents against the PI3 kinase include but are not limited topilaralisib, idelalisib, buparlisib, and IPI-549. In some embodiments, the PI3K inhibitor is selective for PI3K alpha, PI3K beta, PI3K gamma or PI3K delta. Inhibitors of mTOR such as rapamycin, sirolimus, temsirolimus, and everolimus may be combined with TAM kinases inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), PARP (e.g., olaparib), and proteasomes (e.g., bortezomib, carfilzomib) can also be combined with compounds of the present disclosure. In some embodiments, the JAK inhibitor is selective for JAK1 over JAK2 and JAK3. Agents against Pim kinases include but not limited to LGH447, INCB053914, and SGI-1776.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present disclosure include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) inhibitor.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents include CSF1R inhibitors (PLX3397, LY3022855, etc.) and CSF1R antibodies (IMC-054, RG7155, etc).

Other anti-cancer agents include BET inhibitors (INCB054329, OTX015, CPI-0610, etc.), LSD1 inhibitors (GSK2979552, INCB059872, etc), HDAC inhibitors (panobinostat, vorinostat, etc), DNA methyl transferase inhibitors (azacitidine and decitabine), and other epigenetic modulators.

Other anti-cancer agents include Bcl2 inhibitor ABT-199, and other Bcl-2 family protein inhibitors.

Other anti-cancer agents include TGF beta receptor kinase inhibitor such as LY2157299.

Other anti-cancer agents include BTK inhibitor such as ibrutinib.

Other anti-cancer agents include beta catenin pathway inhibitors, notch pathway inhibitors and hedgehog pathway inhibitors.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

One or more additional immune checkpoint inhibitors can be used in combination with a compound as described herein for treatment of TAM-associated diseases, disorders or conditions. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, CD96 TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µs/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the TAM kinases in tissue samples, including human, and for identifying TAM kinases ligands by inhibition binding of a labeled compound. Accordingly, the present invention includes TAM kinases assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$ The radionuclide that is incorporated in the instant radio-labeled compounds will depend on the specific application of that radio-labeled compound. For example, for in vitro TAM kinases labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the TAM kinases. Accordingly, the ability of a test compound to compete with the radio-labeled compound for binding to the TAM kinases directly correlates to its binding affinity.

Kits

The present invention also includes pharmaceutical kits useful, for example, in the treatment or prevention of TAM-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters)(Bridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1 trans-4-[3-(Butylamino)-8-(morpholin-4-ylmethyl)pyrimido[4,5-c]isoquinolin-5(6H)-yl]cyclohexanol

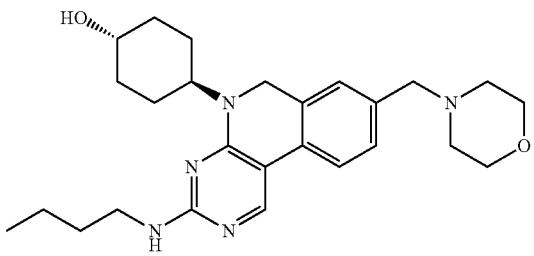 [SMILES: CCCCNc1ncc2c(n1)N([C@H]1CC[C@H](O)CC1)Cc1cc(CN3CCOCC3)ccc1-2]

Step 1: trans-4-{[5-Bromo-2-(butylamino)pyrimidin-4-yl]amino}cyclohexanol

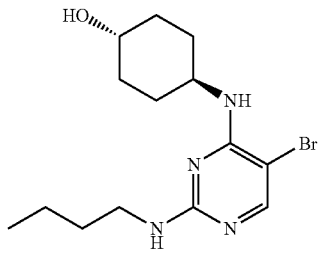 [SMILES: CCCCNc1ncc(Br)c(N[C@H]2CC[C@H](O)CC2)n1]

To a stirred solution of 5-bromo-2, 4-dichloropyrimidine (2.55 g, 11.2 mmol, Sigma-Aldrich, catalog No. 416762) in 1, 4-dioxane (10 mL) were added N,N-diisopropylethylamine (3.33 g, 25.7 mmol), trans-4-aminocyclohexanol hydrochloride (1.73 g, 11.4 mmol, Sigma-Aldrich, catalog No. 263761). The reaction mixture was stirred at 90° C. for 5 h. It was then cooled to room temperature and 1-butanamine (2.4 g, 34.0 mmol) was added. The resulting reaction mixture was stirred at 90° C. for 12 h. After which time the reaction mixture was cooled to room temperature, the solution was concentrated in vacuo and purified by column chromatography (gradient elution with EtOAc in CH$_2$Cl$_2$, 10-50%) to provide trans-4-{[5-bromo-2-(butylamino)pyrimidin-4-yl]amino}cyclohexanol (3.2 g, 83%) as colorless solid. LC-MS calculated for C$_{14}$H$_{24}$BrN$_4$O (M+H)$^+$ m/z: 343.1. found 343.0.

Step 2: 3-(Butylamino)-8-chloro-5-(trans-4-hydroxycyclohexyl)pyrimido[4,5-c]isoquinolin-6(5H)-one

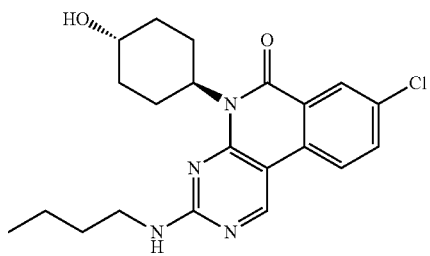 [SMILES: CCCCNc1ncc2c3ccc(Cl)cc3c(=O)n([C@H]3CC[C@H](O)CC3)c2n1]

To a solution of trans-4-{[5-bromo-2-(butylamino)pyrimidin-4-yl]amino}cyclohexanol (0.98 g, 2.8 mmol), 5-chloro-2-(4,4,5,5-tetramethyl-1,3,2-dioxaborolan-2-yl)benzonitrile (0.750 g, 2.84 mmol, Combi-blocks, catalog No. FA-2286), cesium carbonate (1.8 g, 5.7 mmol) in 1, 4-dioxane (21.0 mL) and water (7.0 mL) was added (2'-aminobiphenyl-2-yl)(chloro) [dicyclohexyl(2',4',6'-triisopropylbiphenyl-2-yl)phosphoranylidene]palladium (Sigma-Aldrich, catalog No. 741825, 220 mg, 0.28 mmol). The reaction mixture was kept under N$_2$ at 120° C. for 36 h before it was cooled and extracted with EtOAc. The combined organic layers were dried over Na$_2$SO$_4$, concentrated in vacuo and purified by column chromatography (gradient elution with EtOAc in DCM 10%-50%) to provide 3-(butylamino)-8-chloro-5-(trans-4-hydroxycyclohexyl)pyrimido[4,5-c]isoquinolin-6(5H)-one (115 mg, 10%) as yellow oil. LC-MS calculated for C$_{21}$H$_{26}$ClN$_4$O$_2$ (M+H)$^+$ m/z: 401.2. found 401.1.

Step 3: 3-(Butylamino)-5-(trans-4-hydroxycyclohexyl)-8-vinylpyrimido[4,5-c]isoquinolin-6(5H)-one

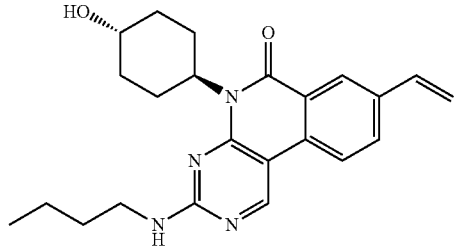 [SMILES: C=Cc1ccc2c(c1)c(=O)n([C@H]1CC[C@H](O)CC1)c1nc(NCCCC)ncc21]

To a solution of 3-(butylamino)-8-chloro-5-(trans-4-hydroxycyclohexyl)pyrimido[4,5-c]isoquinolin-6(5H)-one (800 mg, 2.0 mmol), 4, 4, 5, 5-tetramethyl-2-vinyl-1,3,2-dioxaborolane (920 mg, 6.0 mmol, Sigma-Aldrich, catalog No. 633348), cesium carbonate (1.3 g, 4.0 mmol) in 1, 4-dioxane (12.0 mL) and water (3.0 mL) was added (2'-aminobiphenyl-2-yl)(chloro)-[dicyclohexyl(2',4',6'-triisopropylbiphenyl-2-yl)phosphoranylidene]palladium (80 mg, 0.1 mmol). The reaction mixture was stirred under nitrogen at 90° C. for 3 h before it was cooled and extracted with EtOAc. The combined organic layers were dried over Na$_2$SO$_4$, concentrated in vacuo and purified by column chromatography (gradient elution with EtOAc in DCM, 10%-50%) to afford the olefin (0.64 g, 82%) as a white solid. LC-MS calculated for C$_{23}$H$_{29}$N$_4$O$_2$ (M+H)$^+$ m/z: 393.2. found 393.3.

Step 4: 3-(Butylamino)-5-(trans-4-hydroxycyclohexyl)-6-oxo-5, 6-dihydropyrimido[4,5-c]isoquinoline-8-carbaldehyde

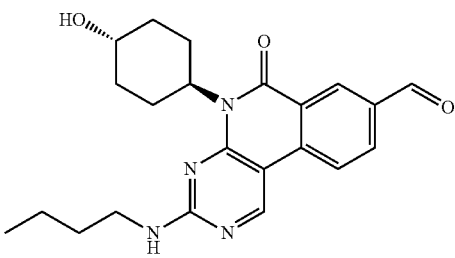 [SMILES: CCCCNc1ncc2c3ccc(C=O)cc3c(=O)n([C@H]3CC[C@H](O)CC3)c2n1]

The olefin obtained above (640 mg, 1.63 mmol) was dissolved in 1, 4-dioxane (9.0 mL) and water (3.0 mL), osmium tetraoxide (2.5% in tert-butanol, 200 mg, 0.020 mmol) and sodium periodate (1300 mg, 6.0 mmol) were added. The resulting reaction mixture was stirred for 2 h before the reaction was quenched with sodium sulfide solution. The mixture was extracted with EtOAc, dried over Na$_2$SO$_4$ and concentrated in vacuo. The crude aldehyde was used without further purification. LC-MS calculated for C$_{22}$H$_{27}$N$_4$O$_3$ (M+H)$^+$ m/z: 395.2. found 395.1.

Step 5: 3-(Butylamino)-5-(trans-4-hydroxycyclohexyl)-8-(morpholin-4-ylmethyl)pyrimido[4,5-c]isoquinolin-6(5H)-one

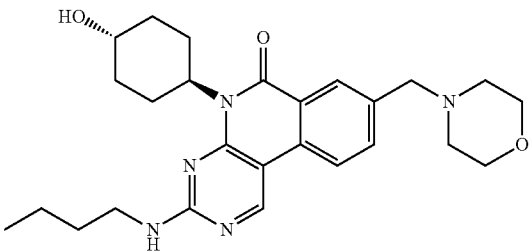 [SMILES: CCCCNc1ncc2c3ccc(CN4CCOCC4)cc3c(=O)n([C@H]3CC[C@H](O)CC3)c2n1]

To a solution of 3-(butylamino)-5-(trans-4-hydroxycyclohexyl)-6-oxo-5,6-dihydropyrimido[4,5-c]isoquinoline-8-carbaldehyde (100 mg, 0.254 mmol) in ethanol (3.0 mL) were added morpholine (110 mg, 1.3 mmol) and acetic acid (76 mg, 1.3 mmol). The resulting reaction mixture was stirred at 90° C. for 2 h before it was cooled to room temperature and sodium cyanoborohydride (48 mg, 0.76 mmol) was added. The reaction mixture was stirred for another 2 h at room temperature before the reaction was quenched with sodium bicarbonate solution and extracted with EtOAc. The combined organic layers were dried over Na$_2$SO$_4$, and concentrated in vacuo. The residue was purified by column chromatography (gradient elution with EtOAc in DCM, 10-90%) to afford 3-(butylamino)-5-(trans-4-hydroxycyclohexyl)-8-(morpholin-4-ylmethyl)pyrimido[4,5-c]isoquinolin-6(5H)-one (38 mg, 32%) as a yellow solid. LC-MS calculated for $C_{26}H_{36}N_5O_3$ $(M+H)^+$ m/z: 466.3. found 466.2.

Step 6: trans-4-[3-(Butylamino)-8-(morpholin-4-ylmethyl)pyrimido[4,5-c]isoquinolin-5(6H)-yl]cyclohexanol To a solution of 3-(butylamino)-5-(trans-4-hydroxycyclohexyl)-8-(morpholin-4-ylmethyl) pyrimido[4,5-c]isoquinolin-6(5H)-one (76 mg, 0.164 mmol) in tetrahydrofuran (2.0 mL) was added lithium tetrahydroaluminate (57 mg, 1.5 mmol). The resulting mixture was stirred at room temperature for 12 h before it was quenched with methanol and purified by RP-HPLC (pH 10) to afford trans-4-[3-(butylamino)-8-(morpholin-4-ylmethyl)pyrimido[4,5-c]isoquinolin-5(6H)-yl]cyclohexanol as white solid. LC-MS calculated for $C_{26}H_{38}N_5O_2$ $(M+H)^+$ m/z: 452.3. found 452.2.

Example 2

3-(Butylamino)-8-[(cyclohexylamino)methyl]-5-(trans-4-hydroxycyclohexyl)pyrimido[4,5-c]isoquinolin-6(5H)-one

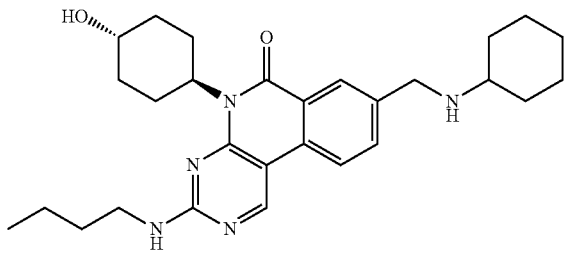 [SMILES: CCCCNc1ncc2c3ccc(CNC4CCCCC4)cc3c(=O)n([C@H]3CC[C@H](O)CC3)c2n1]

To a solution of 3-(butylamino)-5-(trans-4-hydroxycyclohexyl)-6-oxo-5,6-dihydropyrimido[4,5-c]isoquinoline-8-carbaldehyde (Prepared in Example 1, Step 4, 100.0 mg, 0.254 mmol) in ethanol (3.0 mL, 51 mmol) were added cyclohexanamine (120 mg, 1.3 mmol) and acetic acid (76 mg, 1.3 mmol). The resulting reaction mixture was stirred at 90° C. for 2 h before it was cooled to room temperature and sodium cyanoborohydride (48 mg, 0.76 mmol) was added. The reaction mixture was stirred for another 2 h at room temperature before it was quenched with sodium bicarbonate solution and extracted with EtOAc, dried over $Na_2SO_4$, and concentrated in vacuo. The residue was purified by column chromatography (gradient elution with EtOAc in DCM, 10-90%) to afford 3-(butylamino)-8-[(cyclohexylamino)methyl]-5-(trans-4-hydroxycyclohexyl)pyrimido[4,5-c]isoquinolin-6(5H)-one (80 mg, 66%) as white solid. LC-MS calculated for $C_{28}H_{40}N_5O_2$ $(M+H)^+$ m/z: 478.3. found 478.3.

Example 3 trans-4-[3-(Butylamino)-8-[(cyclohexylamino)methyl]pyrimido[4,5-c]isoquinolin-5(6H)-yl]cyclohexanol

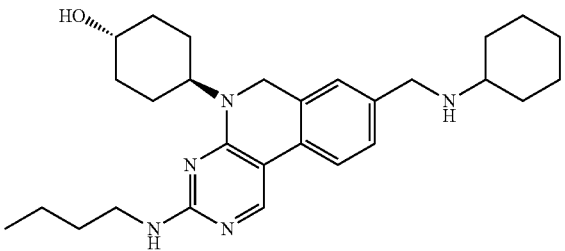 [SMILES: CCCCNc1ncc2c(n1)N([C@H]1CC[C@H](O)CC1)Cc1cc(CNC3CCCCC3)ccc1-2]

To a solution of 3-(butylamino)-8-[(cyclohexylamino)methyl]-5-(trans-4-hydroxycyclohexyl) pyrimido[4,5-c]isoquinolin-6(5H)-one (Prepared in Example 2, 80 mg, 0.167 mmol) in tetrahydrofuran (2.0 mL) was added lithium tetrahydroaluminate (56 mg, 1.5 mmol). The resulting reaction mixture was stirred at room temperature for 12 h before it was quenched with methanol and purified by RP-HPLC (pH 10) to afford trans-4-[3-(Butylamino)-8-[(cyclohexylamino)methyl]pyrimido[4,5-c]isoquinolin-5(6H)-yl]cyclohexanol as colorless solid. LC-MS calculated for $C_{28}H_{42}N_5O$ $(M+H)^+$ m/z: 464.3. found 464.4.

Example 4

3-(Butylamino)-5-(trans-4-hydroxycyclohexyl)-8-[(tetrahydro-2H-pyran-4-ylamino) methyl]pyrimido[4,5-c]isoquinolin-6(5H)-one

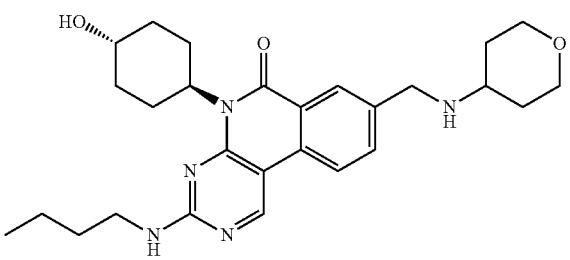 [SMILES: CCCCNc1ncc2c3ccc(CNC4CCOCC4)cc3c(=O)n([C@H]3CC[C@H](O)CC3)c2n1]

This compound was prepared according to the methods described in Example 1 from 3-(Butylamino)-5-(trans-4-hydroxycyclohexyl)-6-oxo-5,6-dihydropyrimido[4,5-c]isoquinoline-8-carbaldehyde (Prepared in Step 4) with tetrahydro-2H-pyran-4-amine replacing morpholine as starting material in Step 5. LC-MS calculated for $C_{27}H_{38}N_5O_3$ $(M+H)^+$ m/z: 480.3. found 480.2.

Example 5

3-(Butylamino)-5-(trans-4-hydroxycyclohexyl)-8-{[(2-hydroxyethyl)amino]methyl}pyrimido[4,5-c]isoquinolin-6(5H)-one

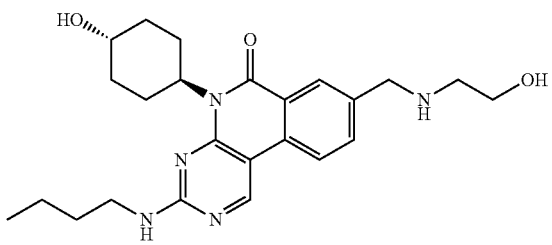 [SMILES: CCCCNc1ncc2c3ccc(CNCCO)cc3c(=O)n([C@H]3CC[C@H](O)CC3)c2n1]

This compound was prepared according to the methods described in Example 1 from 3-(Butylamino)-5-(trans-4-hydroxycyclohexyl)-6-oxo-5,6-dihydropyrimido[4,5-c]isoquinoline-8-carbaldehyde (Prepared in Step 4) with ethanolamine replacing morpholine as starting material in Step 5. LC-MS calculated for $C_{24}H_{34}N_5O_3$, $(M+H)^+$ m/z: 440.3. found 440.2.

Example 6

5-(trans-4-aminocyclohexyl)-3-(butylamino)-8-((cyclohexylamino)methyl)pyrimido[4,5-c]isoquinolin-6(5H)-one

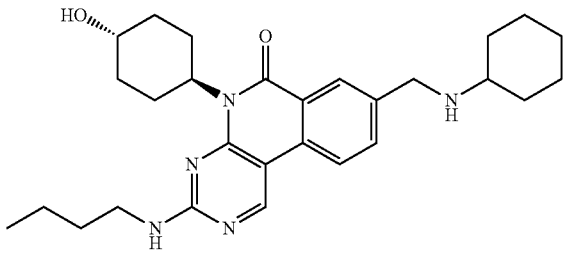 [SMILES: CCCCNc1ncc2c3ccc(CNC4CCCCC4)cc3c(=O)n([C@H]3CC[C@H](O)CC3)c2n1]

Step 1: tert-Butyl {trans-4-[3-(butylamino)-8-[(cyclohexylamino)methyl]-6-oxopyrimido[4,5-c]isoquinolin-5(6H)-yl]cyclohexyl}carbamate

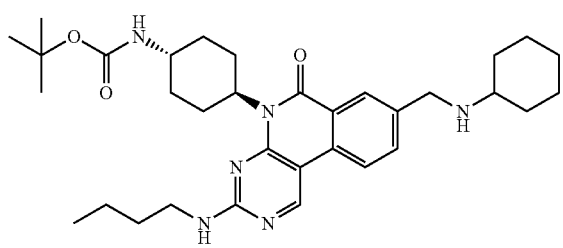 [SMILES: CCCCNc1ncc2c3ccc(CNC4CCCCC4)cc3c(=O)n([C@H]3CC[C@H](NC(=O)OC(C)(C)C)CC3)c2n1]

This compound was prepared by the same method as Example 1 with tert-butyl (trans-4-aminocyclohexyl)carbamate replacing trans-4-aminocyclohexanol hydrochloride as starting material in Step 1, Example 1. LC-MS calculated for $C_{33}H_{49}N_6O_3$ $(M+H)^+$ m/z: 577.4. found 577.5.

Step 2: 5-(trans-4-Aminocyclohexyl)-3-(butylamino)-8-[(cyclohexylamino)methyl]pyrimido[4,5-c]isoquinolin-6(5H)-one To a solution of tert-butyl {trans-4-[3-(butylamino)-8-[(cyclohexylamino)methyl]-6-oxopyrimido[4,5-c]isoquinolin-5(6H)-yl]cyclohexyl}carbamate (50 mg, 0.09 mmol) in dichloromethane (1.0 mL) was added trifluoroacetic acid (0.07 mL, 0.9 mmol). The reaction mixture was stirred at 50° C. for 1 h before it was concentrated in vacuo. The residue was dissolved in methanol and purified by RP-HPLC (pH 10) to afford the 5-(trans-4-aminocyclohexyl)-3-(butylamino)-8-[(cyclohexylamino)methyl]pyrimido[4,5-c]isoquinolin-6(5H)-one as colorless solid. LC-MS calculated for $C_{28}H_{41}N_6O$ $(M+H)^+$ m/z: 477.3. found 477.3.

Example 7

3-(Butylamino)-5-(trans-4-hydroxycyclohexyl)-8-(1-methyl-1H-pyrazol-4-yl)pyrimido[4,5-c]isoquinolin-6(5H)-one

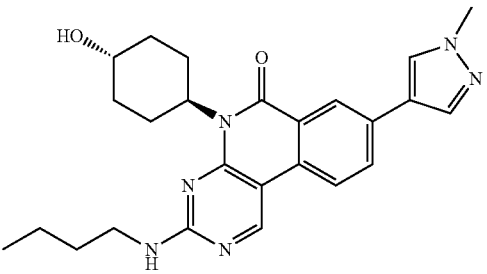 [SMILES: CCCCNc1ncc2c3ccc(-c4cnn(C)c4)cc3c(=O)n([C@H]3CC[C@H](O)CC3)c2n1]

To a solution of 3-(butylamino)-8-chloro-5-(trans-4-hydroxycyclohexyl)pyrimido[4,5-c]isoquinolin-6(5H)-one (Prepared in Example 1, Step 2, 80 mg, 0.20 mmol), 1-methyl-4-(4,4,5,5-tetramethyl-1,3,2-dioxaborolan-2-yl)-1H-pyrazole (62.3 mg, 0.299 mmol, Sigma-Aldrich, catalog No. 595314), cesium carbonate (130 mg, 0.40 mmol) in 1,4-dioxane (1.2 mL) and water (0.3 mL) was added (2'-aminobiphenyl-2-yl)(chloro)[dicyclohexyl(2',4',6'-triisopropylbiphenyl-2-yl)phosphoranylidene] palladium (16 mg, 0.020 mmol). The reaction mixture was stirred under nitrogen at 90° C. for 3 h before it was quenched with methanol and purified by RP-HPLC (pH 10) to afford 3-(butylamino)-5-(trans-4-hydroxycyclohexyl)-8-(1-methyl-1H-pyrazol-4-yl)pyrimido[4,5-c]isoquinolin-6(5H)-one. LC-MS calculated for $C_{25}H_{31}N_6O_2$ $(M+H)^+$ m/z: 447.2. found 447.2.

Example 8

3-(Butylamino)-8-(2, 6-difluorophenyl)-5-(trans-4-hydroxycyclohexyl)pyrimido[4,5-c]isoquinolin-6(5H)-one

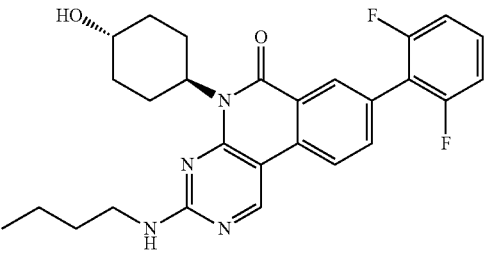 [SMILES: CCCCNc1ncc2c3ccc(-c4c(F)cccc4F)cc3c(=O)n([C@H]3CC[C@H](O)CC3)c2n1]

To a solution of 3-(butylamino)-8-chloro-5-(trans-4-hydroxycyclohexyl)pyrimido[4,5-c]isoquinolin-6(5H)-one (Prepared in Example, Step 2, 80 mg, 0.20 mmol), (2,6-difluorophenyl)boronic acid (47.3 mg, 0.299 mmol, Sigma-Aldrich, catalog No. 470791), cesium carbonate (130 mg, 0.40 mmol) in 1,4-dioxane (1.2 mL) and water (0.3 mL) was added (2'-aminobiphenyl-2-yl)(chloro) [dicyclohexyl(2',4',6'-triisopropylbiphenyl-2-yl)phosphoranylidene] palladium (16 mg, 0.020 mmol). The reaction mixture was stirred under nitrogen at 90° C. for 3 h before the reaction mixture was diluted with methanol and purified by RP-HPLC (pH 10) to afford 3-(butylamino)-8-(2,6-difluorophenyl)-5-(trans-4-hydroxycyclohexyl) pyrimido[4,5-c]isoquinolin-6(5H)-one. LC-MS calculated for $C_{27}H_{29}F_2N_4O_2$ $(M+H)^+$ m/z: 479.2. found 479.3.

Example 9

5-(trans-4-Aminocyclohexyl)-N-butyl-8-[(cyclohexylamino)methyl]-5,6-dihydropyrimido [4,5-c]isoquinolin-3-amine

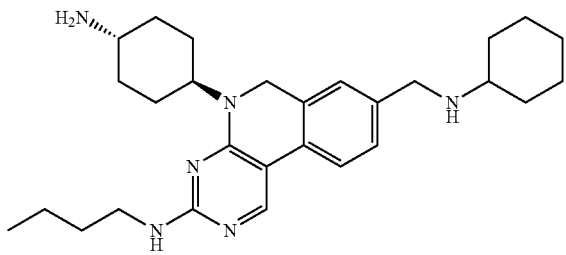 [SMILES: CCCCNc1ncc2c(n1)N([C@H]1CC[C@H](N)CC1)Cc1cc(CNC3CCCCC3)ccc1-2]

Step 1: tert-Butyl [trans-4-({2-(butylamino)-5-[4-chloro-2-(hydroxymethyl)phenyl]pyrimidin-4-yl}amino)cyclohexyl]carbamate

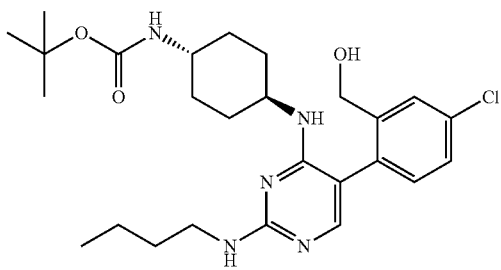 [SMILES: CCCCNc1ncc(-c2ccc(Cl)cc2CO)c(N[C@H]2CC[C@H](NC(=O)OC(C)(C)C)CC2)n1]

To a solution of 2-[2-(bromomethyl)-4-chlorophenyl]-4,4,5,5-tetramethyl-1,3,2-dioxaborolane (611 mg, 1.84 mmol, Combi-blocks, catalog No. PN-3935), tert-butyl (trans-4-{[5-bromo-2-(butylamino)pyrimidin-4-yl]amino}cyclohexyl)carbamate (Prepared as in Example 1, Step 1 using tert-butyl (trans-4-aminocyclohexyl)carbamate as a starting material; 680 mg, 1.54 mmol) in 1, 4-dioxane (20 mL) and water (20 mL) were added potassium carbonate (640 mg, 4.6 mmol) and 4-(di-tert-butylphosphino)-N,N-dimethylaniline-dichloropalladium (2:1) (110 mg, 0.15 mmol, Sigma-Aldrich, catalog No. 678740). The reaction mixture was heated to 90° C. under $N_2$ for 2 h before it was concentrated in vacuo and purified on silica gel column (gradient elution with EtOAc in DCM, 10%400%) to afford tert-butyl [trans-4-({2-(butylamino)-5-[4-chloro-2-(hydroxymethyl)phenyl]pyrimidin-4-yl}amino) cyclohexyl]carbamate (540 mg, 70%). LC-MS calculated for $C_{26}H_{39}ClN_5O_3$ $(M+H)^+$ m/z: 504.3. found 504.2.

Step 2: tert-Butyl {trans-4-[3-(butylamino)-8-chloropyrimido[4,5-c]isoquinolin-5(6H)-yl]cyclohexyl}carbamate

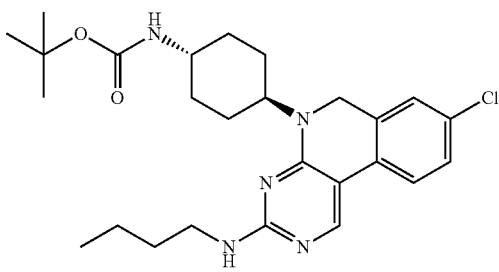 [SMILES: CCCCNc1ncc2c(n1)N([C@H]1CC[C@H](NC(=O)OC(C)(C)C)CC1)Cc1cc(Cl)ccc1-2]

To a solution of tert-butyl [trans-4-({2-(butylamino)-5-[4-chloro-2-(hydroxymethyl)phenyl] pyrimidin-4-yl}amino)cyclohexyl]carbamate (50 mg, 0.099 mmol) in methylene chloride (2.0 mL) were added sodium bicarbonate (42 mg, 0.50 mmol) and Dess-Martin periodinane (84 mg, 0.20 mmol). The resulting reaction mixture was stirred for 3 h before it was concentrated in vacuo. The crude mixture was dissolved in ethanol (1.0 mL), and to this solution were added acetic acid (18 mg, 0.30 mmol) and sodium cyanoborohydride (19 mg, 0.30 mmol). The reaction mixture was stirred for another 2 h before the reaction was quenched with sodium bicarbonate solution and extracted with EtOAc. The organic layers were combined, concentrated and purified by silica gel column (gradient elution with EtOAc in DCM, 10-100%) to afford tert-butyl {trans-4-[3-(butylamino)-8-chloropyrimido[4,5-c]isoquinolin-5(6H)-yl] cyclohexyl}carbamate (31 mg, 64%) as a yellow solid. LC-MS calculated for $C_{26}H_{37}ClN_5O_2$ $(M+H)^+$ m/z: 486.3. found 486.3.

Step 3: tert-Butyl {trans-4-[3-(butylamino)-8-vinylpyrimido[4,5-c]isoquinolin-5(6H)-yl]cyclohexyl} carbamate

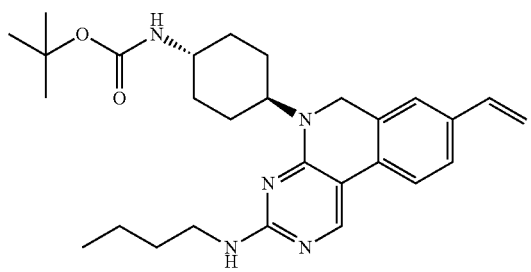 [SMILES: C=Cc1ccc2c(c1)CN([C@H]1CC[C@H](NC(=O)OC(C)(C)C)CC1)c1nc(NCCCC)ncc1-2]

To a solution of tert-butyl {trans-4-[3-(butylamino)-8-chloropyrimido[4,5-c]isoquinolin-5(6H)-yl] cyclohexyl}carbamate (126 mg, 0.26 mmol) and 4,4,5,5-tetramethyl-2-vinyl-1,3,2-dioxaborolane (120 mg, 0.78 mmol) in 1,4-dioxane (2.5 mL) and water (2.5 mL) were added potassium carbonate (110 mg, 0.78 mmol) and 4-(di-tert-butylphosphino)-N,N-dimethylaniline-dichloropalladium (2:1) (18 mg, 0.026 mmol). The reaction was stirred under N$_2$ at 90° C. for 2 h before it was concentrated in vacuo and purified by silica gel column chromatography (gradient elution with EtOAc in DCM, 10%-100%) to afford tert-butyl {trans-4-[3-(butylamino)-8-vinylpyrimido[4,5-c]isoquinolin-5(6H)-yl]cyclohexyl} carbamate (84 mg, 68%) as colorless oil. LC-MS calculated for $C_{28}H_{40}N_5O_2$ (M+H)$^+$ m/z: 478.3. found 478.3.

Step 4: tert-Butyl {trans-4-[3-(butylamino)-8-formylpyrimido[4,5-c]isoquinolin-5(6H)-yl]cyclohexyl}carbamate

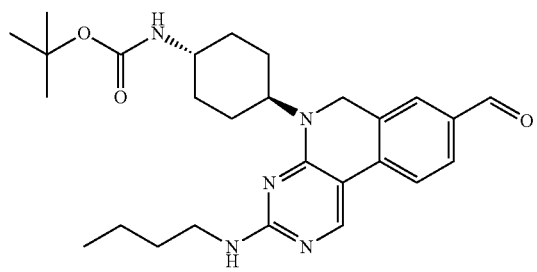 [SMILES: CCCCNc1ncc2c(n1)N([C@H]1CC[C@H](NC(=O)OC(C)(C)C)CC1)Cc1cc(C=O)ccc1-2]

To a solution of tert-butyl {trans-4-[3-(butylamino)-8-vinylpyrimido[4,5-c]isoquinolin-5(6H)-yl]cyclohexyl} carbamate (84 mg, 0.176 mmol) in 1, 4-dioxane (3 mL) and water (1 mL) were added osmium tetraoxide (2.5% in tert-butanol, 190 mg, 0.018 mmol) and sodium periodate (110 mg, 0.50 mmol). The resulting reaction mixture was stirred for 2 h before the reaction was quenched with sodium sulfide solution. The reaction mixture was extracted with EtOAc, dried over Na$_2$SO$_4$ and concentrated in vacuo. The crude aldehyde was used without further purification. LC-MS calculated for $C_{27}H_{38}N_5O_3$ (M+H)$^+$ m/z: 480.3. found 480.3.

Step 5: tert-Butyl {trans-4-[3-(butylamino)-8-[(cyclohexylamino)methyl]pyrimido[4,5-c]isoquinolin-5(6H)-yl]cyclohexyl}carbamate

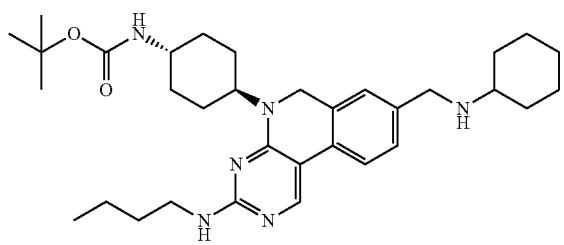 [SMILES: CCCCNc1ncc2c(n1)N([C@H]1CC[C@H](NC(=O)OC(C)(C)C)CC1)Cc1cc(CNC3CCCCC3)ccc1-2]

To a solution of tert-butyl {trans-4-[3-(butylamino)-8-formylpyrimido[4,5-c]isoquinolin-5(6H)-yl]cyclohexyl}carbamate (60 mg, 0.125 mmol) in ethanol (1.2 mL) was added cyclohexylamine (124 mg, 1.25 mmol) and acetic acid (38 mg, 0.62 mmol). The resulting reaction mixture was stirred at 90° C. for 2 h before it was cooled to room temperature and sodium cyanoborohydride (24 mg, 0.38 mmol) was added, and the resultant reaction mixture was stirred at room temperature for another 2 h. The reaction was quenched with sodium bicarbonate solution and extracted with EtOAc. The combined organic layers were dried over Na$_2$SO$_4$, and concentrated in vacuo. The crude amine was used directly without further purification. LC-MS calculated for $C_{33}H_{51}N_6O_2$ (M+H)$^+$ m/z: 563.4. found 563.5.

Step 6: 5-(trans-4-Aminocyclohexyl)-N-butyl-8-[(cyclohexylamino)methyl]-5,6-dihydropyrimido[4,5-c]isoquinolin-3-amine To a solution of tert-Butyl {trans-4-[3-(butylamino)-8-[(cyclohexylamino)methyl]pyrimido[4,5-c]isoquinolin-5(6H)-yl]cyclohexyl}carbamate in methylene chloride (1.0 mL) was added trifluoroacetic acid (0.10 mL, 0.9 mmol). The reaction mixture was stirred at 50° C. for 1 h before it was concentrated in vacuo. The residue was dissolved in methanol and purified by RP-HPLC (pH 2) to afford the title compound as colorless solid. LC-MS calculated for $C_{28}H_{43}N_6$ (M+H)$^+$ m/z: 463.4. found 463.4.

Example 10

5-(trans-4-Aminocyclohexyl)-N-butyl-8-{[(tetrahydropyran-4-yl)amino]methyl}-5,6-dihydropyrimido[4,5-c]isoquinolin-3-amine

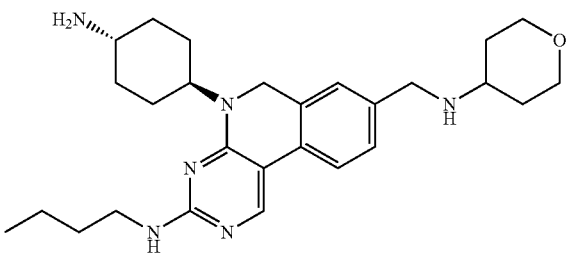 [SMILES: CCCCNc1ncc2c(n1)N([C@H]1CC[C@H](N)CC1)Cc1cc(CNC3CCOCC3)ccc1-2]

This compound was prepared by the same method described in Step 5-6, Example 9 with tetrahydro-2H-pyran-4-amine replacing cyclohexylamine as starting material. LC-MS calculated for $C_{27}H_{41}N_6O$ (M+H)$^+$ m/z: 465.3. found 465.4.

Example 11

5-(trans-4-aminocyclohexyl)-N-butyl-8-((cyclopentylamino)methyl)-5,6-dihydropyrimido[4,5-c]isoquinolin-3-amine

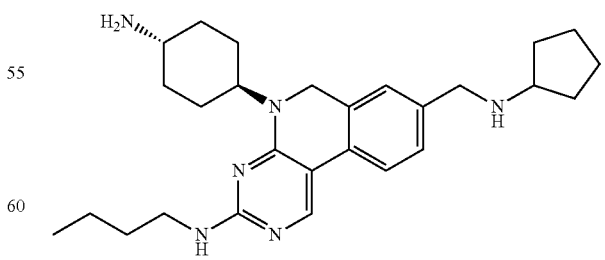

This compound was prepared by the same method described in Step 5-6, Example 9 with cyclopentanamine replacing cyclohexylamine as starting material. LC-MS calculated for $C_{27}H_{41}N_6$ (M+H)$^+$ m/z: 449.3. found 449.2.

Example A

TAM Enzymatic Assay

The assay buffer contained 50 mM HEPES, pH7.5, 10 mM MgCl2, 1 mM EGTA, 0.01% NP-40 and 2 mM DTT. 0.5 ul test compounds dissolved in DMSO were transferred from compound plates to white 384-well assay plates (Greiner LUMITRAC plates). The final concentration of DMSO was 2.5%. Enzyme solutions of 13.8 nM AXL (Life Technologies, PV4275), or 4.1 nM c-MER (Life Technologies, PV4112), or 0.366 nM TYRO3 (Life Technologies, PR7480A) were prepared in assay buffer. A 1 mM stock solution of peptide substrate Biotin-EQEDEPEGDY-FEWLE-amide (Quality Controlled Biochemicals, MA) dissolved in DMSO was diluted to 1 uM in assay buffer containing 100 uM ATP (for AXL and c-MER assays) or 20 uM ATP (for TYRO3 assay). 10 ul enzyme solution (or assay buffer for the enzyme blank) was added to the appropriate wells in each plate, and then 10 ul/well substrate solution was added to initiate the reaction. The plate was protected from light and incubated at room temperature for 60 min. The reaction was stopped by adding 10 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu-W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The compounds of the invention were found to be inhibitors of TAM according to the TAM Enzymatic Assay. Compounds of Formula (I) and all the compounds as described herein have been tested and exhibit an $IC_{50}$ of less than 1 μM.

The compounds of the invention were found to be inhibitors of one or more of AXL, MER, and TYROS. $IC_{50}$ data is provided below in Table 1. The symbol "+" indicates an $IC_{50}$ less than 100 nM, "++" indicates an $IC_{50}$ more than 100 nM but less than 1 μM. "+++" indicates an $IC_{50}$ more than 1 μM.

TABLE 1

| Example No. | AXL IC50 (nM) | MER IC50 (nM) | TYRO3 IC50 (nM) |
| --- | --- | --- | --- |
| 1 | +++ | ++ | ++ |
| 2 | ++ | + | + |
| 3 | + | + | + |
| 4 | +++ | + | ++ |
| 5 | +++ | ++ | ++ |
| 6 | ++ | + | + |
| 7 | +++ | ++ | ++ |
| 8 | +++ | +++ | +++ |
| 9 | + | + | + |
| 10 | ++ | + | + |
| 11 | ++ | + | + |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

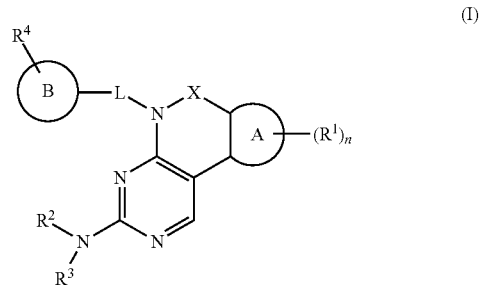

or a pharmaceutically acceptable salt, a tautomer or an isomer thereof, wherein:

ring A is fused $C_{6-10}$ aryl, fused 5- or 6-membered heteroaryl or fused 4 to 10-membered heterocycloalkyl, wherein the fused 5- or 6-membered heteroaryl or fused 4 to 10-membered heterocycloalkyl has a carbon and 1-4 heteroatoms as ring members selected from O, N, and S, wherein the N and S as ring members are each optionally oxidized, with the proviso that ring A is other than pyrazolyl having the formula:

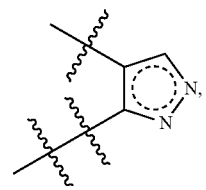

wherein the single wavy line indicates the point of attachment to the X linkage in Formula (I), the double wavy line indicates the point of attachment to the ring carbon atom of the pyrimidine ring in Formula (I) and the dashed circular line indicates a single or a double bond and wherein a ring carbon in pyrazolyl is optionally replaced by a carbonyl group;

ring B is $C_{6-10}$ aryl, 5- or 6-membered heteroaryl, $C_{3-6}$ cycloalkyl or 4 to 10-membered heterocycloalkyl, wherein the 5- or 6-membered heteroaryl or 4 to 10-membered heterocycloalkyl has a carbon and 1-4 heteroatoms as ring members selected from O, N and S, wherein the N and S as ring members are each optionally oxidized and a ring carbon in ring B is optionally replaced by a carbonyl group;

L is a bond, —$(CR^5R^6)_m$—, —C(O)—, —S(O) or —$SO_2$—; $R^5$ and $R^6$ are each independently selected from H, $C_{1-4}$alkyl, $C_{1-4}$ alkoxy, $C_{1-4}$ haloalkyl, $C_{1-4}$ haloalkoxy, halogen, OH, CN and $NH_2$, wherein $C_{1-4}$ alkyl, $C_{1-4}$ alkoxy, $C_{1-4}$ haloalkyl and $C_{1-4}$ haloalkoxy of $R^5$ and $R^6$ are each further optionally substituted with 1-2 members independently selected from halo, OH, CN, $NH_2$, $OR^7$, $NHR^7$, $NR^7R^7$, $C_{1-4}$ alkyl, $C_{1-4}$ alkoxy, $C_{1-4}$ haloalkyl and $C_{1-4}$ haloalkoxy;

or $R^5$ and $R^6$ taken together with the carbon atom to which they are attached form a $C_{3-6}$ cycloalkyl ring, optionally substituted with 1-2 members independently selected from OH, CN, $NH_2$, $OR^7$, $NHR^7$, $NR^7R^7$, $C_{1-4}$alkyl, $C_{1-4}$ alkoxy, $C_{1-4}$ haloalkyl and $C_{1-4}$ haloalkoxy;

each $R^7$ is independently $C_{1-4}$ alkyl;

the subscript m is 1, 2 or 3;

X is a bond, —C(O)— or —CR$^8$R$^9$—;

R$^8$ and R$^9$ are each independently H, $C_{1-4}$ alkyl, $C_{1-4}$ alkoxy, $C_{1-4}$ haloalkyl or $C_{1-4}$ haloalkoxy, wherein the $C_{1-4}$ alkyl, $C_{1-4}$ alkoxy, $C_{1-4}$ haloalkyl and $C_{1-4}$ haloalkoxy of R$^8$ and R$^9$ are each optionally substituted with 1-2 members independently selected from OH, CN, NH$_2$, OR$^7$, NHR$^7$, NR$^7$R$^7$, $C_{1-4}$ alkyl, $C_{1-4}$ alkoxy, $C_{1-4}$ haloalkyl, and $C_{1-4}$ haloalkoxy;

or R$^8$ and R$^9$ taken together with the carbon atom to which they are attached form a $C_{3-6}$ cycloalkyl ring, optionally substituted with 1-2 members independently selected from OH, CN, NH$_2$, OR$^7$, NHR$^7$, NR$^7$R$^7$, $C_{1-4}$ alkyl, $C_{1-4}$ alkoxy, $C_{1-4}$ haloalkyl, and $C_{1-4}$ haloalkoxy;

each R$^1$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NH$_2$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^1$ are each optionally substituted with 1, 2, 3, or 4 R$^b$ substituents;

each R$^b$ is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ and S(O)$_2$NR$^c$R$^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^b$ are each further optionally substituted with 1-3 R$^d$ substituents;

or two R$^1$ substituents attached to the same carbon of ring A are taken together to form an oxo group or a $C_{3-6}$ cycloalkyl optionally substituted with 1-2 members independently selected from OH, CN, NH$_2$, OR$^7$, NHR$^7$, NR$^7$R$^7$, $C_{1-4}$ alkyl, $C_{1-4}$ alkoxy, $C_{1-4}$ haloalkyl, and $C_{1-4}$ haloalkoxy;

each R$^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^a$ are each optionally substituted with 1, 2, 3, 4, or 5 R$^d$ substituents;

each R$^d$ is independently selected from $C_{1-4}$ alkyl, $C_{1-4}$ haloalkyl, halo, CN, R$^e$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NH$_2$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$;

each R$^e$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, 10 aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^c$ are each optionally substituted with 1, 2, 3, 4, or 5 R$^f$ substituents;

each R$^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NH$_2$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, and S(O)$_2$NR$^g$R$^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^f$ are each optionally substituted with 1, 2, 3, 4, or 5 R$^n$ substituents;

each R$^n$ is independently selected from $C_{1-4}$ alkyl, $C_{1-4}$ haloalkyl, halo, CN, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$;

each R$^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^g$ are each optionally substituted with 1-3 R$^p$ substituents;

or any two R$^a$ substituents, together with the nitrogen atom to which they are attached, form a 4-, 5-, 6-, or 7-membered heterocycloalkyl group optionally substituted with 1, 2, or 3 R$^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{1-6}$ haloalkyl, halo, CN, $OR^i$, $R^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, and 5-6 membered heteroaryl of $R^h$ are each further optionally substituted by 1, 2, or 3 substituents;

each $R^j$ independently selected from halo, $C_{1-4}$ alkyl, $C_{1-4}$ haloalkyl, CN, $R^k$, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

or any two $R^c$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^e$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^g$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^i$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^k$ substituents, together with the nitrogen atom to which they are attached, form a 4-, 5-, 6-, or 7-membered heterocycloalkyl group optionally substituted with 1, 2, or 3 independently selected $R^h$ substituents;

or any two $R^o$ substituents, together with the nitrogen atom to which they are attached, form a 4-, 5-, 6-, or 7-membered heterocycloalkyl group optionally substituted with 1, 2, or 3 independently selected $R^h$ substituents;

each $R^e$, $R^i$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl and $C_{2-4}$ alkynyl of $R^e$, $R^i$, $R^k$, $R^o$ or $R^p$ are each optionally substituted with 1, 2, or 3 substituents independently selected from OH, CN, amino, halo, $C_{1-4}$ alkyl, $C_{1-4}$ alkoxy, $C_{1-4}$ alkylthio, $NHR^7$, $NR^7R^7$, $C_{1-4}$ haloalkyl, and $C_{1-4}$ haloalkoxy;

$R^2$ is $C_{1-6}$alkyl optionally substituted with 1-3 independently selected $R^b$ groups;

$R^3$ is H or $C_{1-6}$alkyl;

$R^4$ is $-NH_2$, $-NHOH$, $-OH$, $-CN$, $-COOH$, $C_{1-4}$ alkyl, $C_{1-4}$ alkoxy, $C_{1-2}$ haloalkyl, $C_{1-2}$haloalkoxy, $-NHR^{10}$, $-N(R^{10})_2$, $NHOR^{10}$, $-NHC(O)R^{10}$, $-C(O)R^{10}$, $-C(O)NR^{10}R^{10}$, $-C(O)OR^{10}$, $-OC(O)R^{10}$, $-OC(O)NR^{10}R^{10}$, $-NR^{10}R^{10}$, $-NR^{10}C(O)R^{10}$ or $-NR^{10}C(O)OR^{10}$; wherein the $C_{1-4}$alkyl, $C_{1-4}$ alkoxy, $C_{1-2}$ haloalkyl and $C_{1-2}$ haloalkoxy of $R^4$ are each optionally substituted with 1-3 $R^m$ substituents independently selected from OH, CN, amino, halo, $C_{1-4}$ alkyl, $C_{1-4}$ alkoxy, $C_{1-4}$ alkylthio, $NHR^7$, $NR^7R^7$, $C_{1-4}$ haloalkyl, and $C_{1-4}$ haloalkoxy;

each $R^{10}$ is independently $C_{1-4}$ alkyl, $C_{6-10}$aryl or $C_{1-2}$ haloalkyl, each of which is optionally substituted with 1-2 independently selected $R^f$ groups; and the subscript n is 1, 2 or 3.

2. The compound of claim 1, having Formula (II):

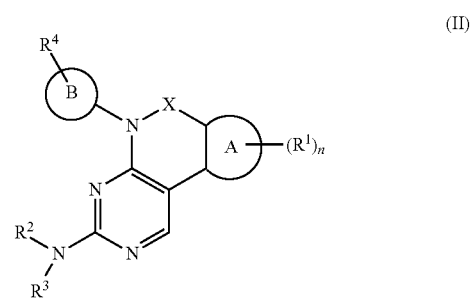

(II)

or a pharmaceutically acceptable salt, a tautomer or an isomer thereof.

3. The compound of claim 1, having Formula (III):

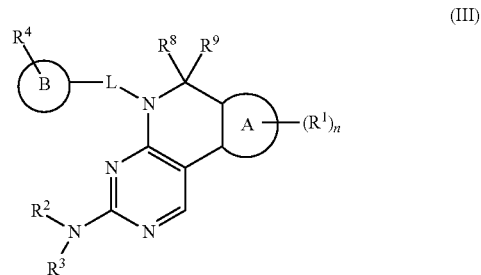

(III)

or a pharmaceutically acceptable salt, a tautomer or an isomer thereof.

4. The compound of claim 1, having Formula (IV):

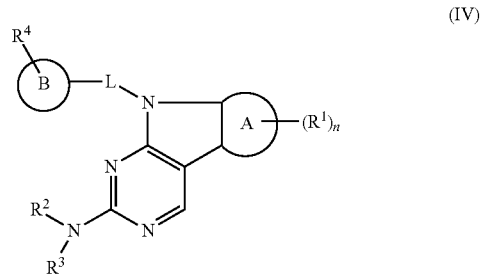

(IV)

or a pharmaceutically acceptable salt, a tautomer or an isomer thereof.

5. The compound of claim 1, or a pharmaceutically acceptable salt, a tautomer or an isomer thereof, wherein ring A is fused phenyl.

6. The compound of claim 1, or a pharmaceutically acceptable salt, a tautomer or an isomer thereof, wherein ring A is a fused 5-membered heteroaryl selected from:

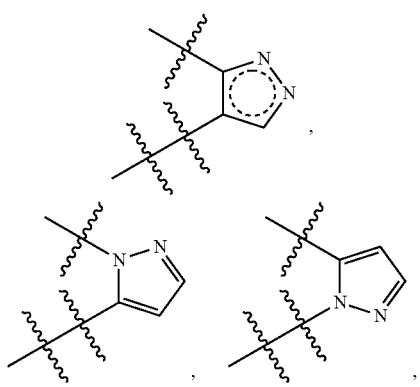

pyrrolyl, imidazolyl, triazolyl, tetrazolyl, oxazolyl, thiazolyl, isoxazolyl, furanyl, thiophenyl, and isothiazolyl.

7. The compound of claim 1, or a pharmaceutically acceptable salt, a tautomer or an isomer thereof, wherein ring A is fused 6-membered heteroaryl selected from pyridyl, pyrimidinyl, pyrazinyl, pyridazinyl, and triazinyl.

8. The compound of claim 1, or a pharmaceutically acceptable salt, a tautomer or an isomer thereof, wherein ring B is cyclopropyl, cyclobutyl, cyclopentyl, or cyclohexyl.

9. The compound of claim 1, or a pharmaceutically acceptable salt, a tautomer or an isomer thereof, wherein ring B is 4 to 7-membered heterocycloalkyl selected from azetidinyl, oxetanyl, pyrrolidinyl, tetrahydrofuranyl, oxazolidinyl, isooxazolidinyl, thiazolidinyl, isothiazolidinyl, tetrahydro-pyranyl, morpholinyl, piperidinyl, piperazinyl, oxepanyl, and azepanyl.

10. The compound of claim 1, or a pharmaceutically acceptable salt, a tautomer or an isomer thereof, wherein L is a bond or —(CH$_2$)$_m$—.

11. The compound of claim 1, or a pharmaceutically acceptable salt, a tautomer or an isomer thereof, wherein X is —CH$_2$— or —C(O)—.

12. The compound of claim 1, or a pharmaceutically acceptable salt, a tautomer or an isomer thereof, wherein:
   each R$^1$ is independently selected from C$_{1-6}$ alkyl, C$_{1-6}$ haloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, each optionally substituted with 1-2 R$^b$ substituents;
   each R$^b$ is independently selected from C$_{1-6}$ alkyl, C$_{1-4}$ haloalkyl, halo, CN, NHOR$^c$, OR$^c$, C(O)NR$^c$R$^c$, C(O)OR$^c$, OC(O)R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, NR$^c$S(O)$_2$R$^c$, NR$^c$S(O)$_2$NR$^c$R$^c$, S(O)$_2$R$^c$, and S(O)$_2$NR$^c$R$^c$;
   each R$^c$ is independently selected from H, C$_{1-6}$ alkyl, C$_{1-4}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{14}$ alkyl- of R$^c$ are each optionally substituted with 1-2 R$^f$ substituents; and
   each R$^f$ substituent is independently selected from F, Cl, OH, C$_{1-4}$ alkoxy, C$_{1-4}$ haloalkoxy, NH$_2$, NH(C$_{1-4}$ alkyl), N(C$_{1-4}$ alkyl)$_2$, C(O)(C$_{1-4}$ alkyl), C(O)NH$_2$, C(O)NH(C$_{1-4}$ alkyl), C(O)N(C$_{1-4}$ alkyl)$_2$, NHC(O)NH$_2$, NHC(O)NH—C$_{1-4}$ alkyl, NHC(O)N(C$_{1-4}$ alkyl)$_2$, OC(O)—C$_{1-4}$ alkyl, NHC(O)—C$_{1-4}$ alkyl, NHS(O)$_2$—C$_{1-4}$ alkyl, S(O)$_2$—C$_{1-4}$ alkyl, S(O)$_2$NH$_2$, S(O)$_2$NH—C$_{1-4}$ alkyl, S(O)$_2$N(C$_{1-4}$ alkyl)$_2$, NHS(O)$_2$NH$_2$, NHS(O)$_2$NH—C$_{1-4}$ alkyl, and NHS(O)$_2$N(C$_{1-4}$ alkyl)$_2$.

13. The compound of claim 1, or a pharmaceutically acceptable salt, a tautomer or an isomer thereof, wherein R$^1$ is C$_{1-6}$alkyl, 5 to 6-membered heteroaryl, 4 to 7-membered heterocycloalkyl-C$_{1-4}$ alkyl or C$_{6-10}$ aryl, each of which is optionally substituted with 1-3 independently selected R$^b$ groups.

14. The compound of claim 1, or a pharmaceutically acceptable salt, a tautomer or an isomer thereof, wherein R$^1$ is C$_{1-6}$alkyl, 5 or 6-membered heteroaryl or phenyl, each of which is substituted with 1-3 independently selected R$^b$ groups.

15. The compound of claim 12, or a pharmaceutically acceptable salt, a tautomer or an isomer thereof, wherein:
   each R$^b$ is independently selected from halo, NR$^c$R$^c$, and C$_{1-6}$ alkyl; and
   each R$^c$ is independently selected from C$_{1-6}$ alkyl, C$_{3-6}$ cycloalkyl, and 4-6 membered heterocycloalkyl; wherein said C$_{1-6}$ alkyl of R$^c$ is optionally substituted with OH.

16. The compound of claim 1, or a pharmaceutically acceptable salt, a tautomer or an isomer thereof, wherein R$^1$ is morpholinylmethyl, cyclohexylaminomethyl, cyclopenylaminomethyl, 4-tetrahydro-2H-pyranylaminomethyl, C$_{1-4}$alkylamino-C$_{1-4}$alkyl, pyrazolyl, imidazolyl, 2-hydroxyethylaminomethyl or phenyl, each of which is optionally substituted with 1-3 members independently selected from OH, CN, amino, halo, C$_{1-4}$ alkyl, C$_{1-4}$ alkoxy, C$_{1-4}$ alkylthio, NHR$^7$, NR$^7$R$^7$, C$_{1-4}$ haloalkyl, and C$_{1-4}$ haloalkoxy.

17. The compound of claim 1, or a pharmaceutically acceptable salt, a tautomer or an isomer thereof, wherein R$^1$ is morpholin-4-ylmethyl, 2-hydroxyethylaminomethyl, cyclopentylaminomethyl, cyclohexylaminomethyl, tetrahydropyran-4-yl-aminomethyl, 1-methylimidazol-4-yl, or 2,6-difluorophenyl.

18. The compound of claim 1, or a pharmaceutically acceptable salt, a tautomer or an isomer thereof, wherein R$^2$ is C$_{1-6}$ alkyl optionally substituted with one R$^b$ group.

19. The compound of claim 1, or a pharmaceutically acceptable salt, a tautomer or an isomer thereof, wherein R$^2$ is n-butyl.

20. The compound of claim 1, or a pharmaceutically acceptable salt, a tautomer or an isomer thereof, wherein R$^3$ is H.

21. The compound of claim 1, or a pharmaceutically acceptable salt, a tautomer or an isomer thereof, wherein R$^4$ is NH$_2$ or OH.

22. The compound of claim 1, or a pharmaceutically acceptable salt, a tautomer or an isomer thereof, wherein the substituents on ring B have trans configuration with respect to each other, when ring B is C$_{3-6}$ cycloalkyl or 4 to 10-membered heterocycloalkyl.

23. The compound of claim 1, wherein the compound is selected from:
   trans-4-[3-(Butylamino)-8-(morpholin-4-ylmethyl)pyrimido[4,5-c]isoquinolin-5(6H)-yl]cyclohexanol;
   3-(Butylamino)-8-[(cyclohexylamino)methyl]-5-(trans-4-hydroxycyclohexyl)pyrimido[4,5-c]isoquinolin-6(5H)-one;
   trans-4-[3-(Butylamino)-8-[(cyclohexylamino)methyl] pyrimido[4,5-c]isoquinolin-5(6H)-yl]cyclohexanol;

3-(Butylamino)-5-(trans-4-hydroxycyclohexyl)-8-[(tetra-hydro-2H-pyran-4-ylamino) methyl]pyrimido[4,5-c]isoquinolin-6(5H)-one;

3-(Butylamino)-5-(trans-4-hydroxycyclohexyl)-8-{[(2-hydroxyethyl)amino]methyl}pyrimido [4,5-c]isoquinolin-6(5H)-one;

5-(trans-4-aminocyclohexyl)-3-(butylamino)-8-((cyclohexylamino)methyl)pyrimido[4,5-c]isoquinolin-6(5H)-one;

3-(Butylamino)-5-(trans-4-hydroxycyclohexyl)-8-(1-methyl-1H-pyrazol-4-yl)pyrimido[4,5-c]isoquinolin-6(5H)-one;

3-(Butylamino)-8-(2, 6-difluorophenyl)-5-(trans-4-hydroxycyclohexyl)pyrimido[4,5-c]isoquinolin-6(5H)-one;

5-(trans-4-aminocyclohexyl)-N-butyl-8-[(cyclohexylamino)methyl]-5,6-dihydropyrimido [4,5-c]isoquinolin-3-amine;

5-(trans-4-Aminocyclohexyl)-N-butyl-8-{[(tetrahydropyran-4-yl)amino]methyl}-5, 6-dihydropyrimido[4,5-c]isoquinolin-3-amine; and 5-(trans-4-aminocyclohexyl)-N-butyl-8-((cyclopentylamino)methyl)-5,6-dihydropyrimido[4,5-c]isoquinolin-3-amine;

or a pharmaceutically acceptable salt thereof.

24. A pharmaceutical composition comprising a compound of claim 1, or a pharmaceutically acceptable salt, a tautomer or an isomer thereof, and a pharmaceutically acceptable carrier or excipient.

25. A method for inhibiting TAM kinases, said method comprising: contacting the TAM kinases with a compound of claim 1, or a pharmaceutically acceptable salt, a tautomer or an isomer thereof.

26. A method for inhibiting or ameliorating cancer in a patient, said method comprising: administering to the patient a therapeutically effective amount of a compound of claim 1, or a pharmaceutically acceptable salt, a tautomer or an isomer thereof.

27. The method of claim 26, wherein the cancer is selected from hepatocellular cancer, bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

28. The method of claim 26, wherein the cancer is lung cancer, prostate cancer, colon cancer, breast cancer, melanoma, renal cell carcinoma, multiple myeloma, gastric cancer, or rhabdomyosarcoma.

* * * * *

UNITED STATES PATENT AND TRADEMARK OFFICE
CERTIFICATE OF CORRECTION

PATENT NO. : 9,840,503 B2
APPLICATION NO. : 15/151259
DATED : December 12, 2017
INVENTOR(S) : Yaping Sun, Yun-Long Li and David M. Burns It is certified that error appears in the above-identified patent and that said Letters Patent is hereby corrected as shown below:

In the Claims

Column 64, Line 19, Claim 1, delete "10 aryl," and insert -- $C_{6-10}$ aryl, --;

Column 68, Lines 28-29, Claim 16, delete "cyclopenylaminomethyl," and insert -- cyclopentylaminomethyl, --;

Column 69, Line 2, Claim 23, delete "ylamino) methyl]" and insert -- ylamino)methyl] --;

Column 69, Line 5, Claim 23, delete "pyrimido [4,5-c]" and insert -- pyrimido[4,5-c] --;

Column 69, Line 13, Claim 23, delete "(2, 6-" and insert -- (2,6- --;

Column 69, Line 18, Claim 23, delete "dihydropyrimido [4,5-c]" and insert -- dihydropyrimido[4,5-c] --;

Column 69, Line 21, Claim 23, delete "5, 6" and insert -- 5,6 --.

Signed and Sealed this
Twenty-fourth Day of March, 2020

Andrei Iancu
*Director of the United States Patent and Trademark Office*